(12) United States Patent
Ishow et al.

(10) Patent No.: US 9,597,418 B2
(45) Date of Patent: Mar. 21, 2017

(54) MAGNETIC AND FLUORESCENT REVERSE NANOASSEMBLIES

(71) Applicants: UNIVERSITE DE NANTES, Nantes (FR); CENTRE NATIONAL DE LA RECHERCHE SCIENTIFIQUE (CNRS), Paris (FR)

(72) Inventors: Elena Ishow, Nantes (FR); Adrien Faucon, Nantes (FR)

(73) Assignees: UNIVERSITE DE NANTES, Nantes (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/218,368

(22) Filed: Mar. 18, 2014

(65) Prior Publication Data
US 2015/0265728 A1    Sep. 24, 2015

(51) Int. Cl.
*A61K 49/18* (2006.01)
*A61K 49/12* (2006.01)
*A61K 41/00* (2006.01)
*A61K 47/48* (2006.01)
*A61K 49/00* (2006.01)

(52) U.S. Cl.
CPC .......... *A61K 49/1878* (2013.01); *A61K 41/00* (2013.01); *A61K 47/48869* (2013.01); *A61K 47/48884* (2013.01); *A61K 49/0002* (2013.01); *A61K 49/0021* (2013.01); *A61K 49/0093* (2013.01); *A61K 49/126* (2013.01)

(58) Field of Classification Search
CPC ............ A61K 49/0023; A61K 49/0067; A61K 31/295; A61K 49/12; A61K 49/18
See application file for complete search history.

(56) References Cited

U.S. PATENT DOCUMENTS

| | | | |
|---|---|---|---|
| 5,395,688 A * | 3/1995 | Wang | B01J 8/008 252/301.35 |
| 6,207,134 B1 * | 3/2001 | Fahlvik | A61K 49/1854 424/9.322 |
| 8,236,284 B1 | 8/2012 | Perez et al. | |
| 2007/0059705 A1 * | 3/2007 | Lu | B82Y 15/00 435/6.11 |
| 2011/0045081 A1 * | 2/2011 | Steitz et al. | 424/489 |
| 2013/0030282 A1 | 1/2013 | Margel et al. | |

OTHER PUBLICATIONS

Adrien Faucon et al. Photoactive chelating organic nanospheres as central platforms of biomodal hybrid nanoparticles, Journal of Materials Chemistry C, 2013, 1, 3879.*

J. Fresnais et al. Reorientation kinetics of superparamagnetic nanostructured rods, J. Phys.: Condens. Matter, 20, 494216, 2008.*
Cheon at al., "Synergistically integrated nanoparticles as multimodal probes for nanobiotechnology", Accounts of Chemical Research, vol. 41, No. 12, 2008, pp. 1630-1640.
Lee et al., "Designed synthesis of uniformly sized iron oxide nanoparticles for efficient magnetic resonance imaging contrast agents", Chem. Soc. Rev., vol. 41, 2012 (first published online on Dec. 2011), pp. 2575-2589.
Fan et al., "Multifunctional plasmonic shell—magnetic core nanoparticles for targeted diagnostics, isolation, and photothermal destruction of tumor cells", ACS Nano, vol. 6, No. 2, Jan. 2012, pp. 1065-1073.
Bigall et al., "Fluorescent, magnetic and plasmonic-hybrid multifunctional colloidal nano objects", Nano Today, vol. 7, Jul. 2012, pp. 282-296.
Faucon et al., "Photoactive chelating organic nanospheres as central platforms of bimodal hybrid nanoparticles", Journal of Materials Chemistry C, vol. 1, Apr. 2013, pp. 3879-3886.
Massart et al., "Preparation of aqueous magnetic liquids in alkaline and acidic media", IEEE Trans. Magn., vol. 17, No. 2, Mar. 1981, pp. 1247-1248.
Doussineau et al., "Charging megadalton poly(ethylene oxide)s by electrospray ionization. A charge detection mass spectrometry study", Rapid Commun. in Mass Spectrom., vol. 25, Jan. 2011, pp. 617-623.
Lee et al., "Dual-Mode Nanoparticle Probes for High-Performance Magnetic Resonance and Fluorescence Imaging of Neuroblastoma", Angew Chem. Int. Ed., vol. 45, No. 48 Dec. 2006, pp. 8160-8162.
Hassan et al., "Continuous Multistep Microfluidic Assisted Assembly of Fluorescent, Plasmonic, and Magnetic Nanostructures", Angew Chem. Int. Ed., vol. 52, No. 7, Feb. 2013, pp. 1994-1997.
Lee et al., "Uniform Mesoporous Dye-Doped Silica Nanoparticles Decorated with Multiple Magnetite Nanocrystals for Simultaneous Enhanced Magnetic Resonance Imaging, Fluorescence Imaging, and Drug Delivery", J. Am. Chem. Soc., vol. 132, No. 2, Jan. 2010, pp. 552-557.
Fresnais et al., "Electrostatic co-assembly of magnetic nanoparticles and fluorescent nanospheres: a versatile approach towards bimodal nanorods", Small, vol. 5, No. 22, Nov. 16, 2009, pp. 2533-2536.
Di Corato et al., "Multifunctional nanobeads based on quantum dots and magnetic nanoparticles: synthesis and cancer cell targeting and sorting", ACS NANO, vol. 5, No. 2, Feb. 22, 2011, pp. 1109-1121.
International Search Report dated Jun. 10, 2015, in corresponding PCT application.

* cited by examiner

*Primary Examiner* — Michael G Hartley
*Assistant Examiner* — Jagadishwar Samala
(74) *Attorney, Agent, or Firm* — Young & Thompson

(57) ABSTRACT

The present invention relates to magnetic and fluorescent nanoassemblies having reverse architectures. Especially, the nanoassemblies of the invention comprise a fluorescent core and magnetic nanoparticles contacting the surface of the fluorescent core. The nanoassemblies of the invention may further be coated by a polymer, which may optionally be functionalized. The invention further relates to a process for manufacturing the nanoassemblies of the invention. The invention is also directed to the use of the nanoassemblies of the invention, especially for multimodal imaging, in vitro and/or in vivo diagnostics through multimodal imaging, and/or therapy.

15 Claims, 6 Drawing Sheets

MAGNETIC AND FLUORESCENT REVERSE NANOASSEMBLIES

FIELD OF INVENTION

The present invention relates to magnetic and fluorescent nanoassemblies having reverse architectures. Especially, the nanoassemblies of the invention comprise a fluorescent core and superparamagnetic nanoparticles at the surface thereof, leading to a core-shell architecture. The nanoassemblies of the invention may further be coated by a polymer, which may optionally be functionalized. The invention further relates to a process for manufacturing the nanoassemblies of the invention. The invention is also directed to the use of the nanoassemblies of the invention, especially for multimodal imaging, in vitro and/or in vivo diagnostics through multimodal imaging, and/or therapy.

BACKGROUND OF INVENTION

Multimodal nanoparticles (NPs) advantageously possess properties such as a size similar to those of proteins or nucleic acids, large interactions due to their high surface area to volume ratio, complementary combination of active units within a single platform, high active material localization, structural diversity, and long circulation time in blood compared to small molecules.

The elaboration of bimodal nanoparticles, combining fluorescence and magnetism, has fostered great interest for their promising potential in dual bioimaging for diagnosis, remote drug vectorization, therapy by hyperthermia and selection of biological entities. While fluorescence detection is characterized by high sensitivity, addressing magnetic properties opens up the possibility of deep tissue imaging and remote mass transfer.

Most of the common systems that have been elaborated so far consist of iron oxide nanoparticles (magnetic), which are known for their relative innocuity, coated with organic or inorganic functional units (fluorescent). Alternative doped or core-shell structures have been elaborated with luminescent lanthanides or quantum dots, and yet these latter structures require prior encapsulation in silica or latex matrices to be protected from emission quenching by the surroundings. (Cheon and Lee, *Acc. Chem. Res.* 2008, 41, 1630-1640; Lee et al., *Chem. Soc. Rev.* 2012, 41, 2575-2589; Fan et al., *ACS Nano* 2012, 6, 1065-1073; Bigall et al., *Nano Today,* 2012, 7, 282-296).

For all these systems, deleterious electron transfer effects exerted by the magnetic nanoparticles on the luminophore emission have been noted, which is reinforced by the usually low payload of luminophores compared to that of iron oxide nanoparticles.

Moreover, these nanoparticles suffer from the following drawbacks:
- leakage or disassembling of the fluorescent molecules or the magnetic nanoparticles, especially in biological media, leading to a loss of combined fluorescence and magnetism, a decrease in the performances, and the appearance of noise signal;
- low payload of fluorescent and magnetic active units, compelling to use high doses;
- high photobleaching yield in the case of individual organic fluorescent molecules;
- high sensitivity of fluorescence towards the biological surroundings causing possible emission quenching or color shift;
- weak size discrimination leading to non-specific targeting of organs and/or malignant cells;
- low half-life in biological media, especially short circulation time in blood causing rapid clearance of materials following intravenous injection;
- difficulties to further functionalize the nanoparticle surface, whereas functionalization brings strong added value in terms of biological targeting and action.

Surprisingly, core-shell structures, based on an organic emissive platform (fluorescent) surrounded by magnetic nanoparticles have never been proposed to address these issues.

The present invention thus relates to nanoassemblies comprising a matrix-free organic fluorescent core surrounded by magnetic nanoparticles. The resulting reverse architecture of the nanoassemblies of the invention resembles a "raspberry like" arrangement (FIG. 1) (Faucon et al., *J. Mater. Chem. C.,* 2013, 1, 3879-3886). In the following, such reverse architectures are referred to as "fluo@mag" nanoassemblies.

The Applicant evidenced that such reverse architectures provide dense emissive core where the embedded fluorescent molecules become insensitive to the pH or the ionic strength of the media, and provide stable fluorescence signal under usual light observation conditions. Moreover, emission quenching from the magnetic nanoparticles through deleterious electron transfer is severely reduced due to effective separation of the magnetic nanoparticles from the fluorescent core. More than 70% of the core's fluorescence is retained after addition of the magnetic nanoparticles. Positioning magnetic nanoparticles on the periphery creates a charged shell structure which acts as a repelling electrostatic barrier to ions or hydrophobic molecules. As a result, fluorescent molecules are protected from possible dissolution in hydrophobic media or action by enzymes, which would result in the disassembling/release of intact or transformed individual fluorescent molecules. This in turn reinforces the fluorescent core cohesion through strong interactions of the fluorescent molecules, hence destabilization upon solvation is unlikely to occur. By contrast, the possible loss of magnetic nanoparticles would cause little effects in terms of spurious signal as the magnetic response of individual nanoparticles is smaller than that of the final bimodal assemblies.

The fluo@mag nanoassemblies of the invention present many advantages as described above. Due to their manufacturing process, illustrated in the experimental part below, they are obtained and stabilized under dilute acidic conditions, preferably using nitric acid. These acidic conditions are not optimized for biological purposes, especially for in vivo imaging. There is thus a need for stabilization of the nanoassemblies of the invention in water and physiological conditions.

Moreover, it would be interesting to functionalize the nanoassemblies of the invention by bioactive molecules in order to widen the range of possible biological applications of the nanoassemblies. Care should be taken that functionalization of the nanoassemblies does not lead to the aggregation of nanoassemblies.

The Applicant evidenced that stabilization in physiological conditions and functionalization may be achieved by the addition of a polymeric protective shell around the nanoassembly of the invention.

Especially, the Applicant showed that coating the surface of the nanoassembly of the invention using a polymer may achieve the above expected effects (FIG. 2). In the following, such fluo@mag nanoassemblies coated with a polymer are referred to as fluo@ mag@polymer nanoassemblies.

The polymer used to modify the nanoassemblies of the invention should meet the following specifications:

Interactions between the polymer and the nanoassembly should provide overall stiff cohesion to the fluo@mag@polymer nanoassembly. For that purpose, electrostatic interactions with the positively charged surface of the nanoassemblies are preferred. Moreover, the polymer preferably comprises a multiplicity of sites interacting with the nanoassembly.

The association constant between the polymer and the magnetic nanoparticles should be lower than the association constant between the fluorescent core and the magnetic nanoparticles. In other words, the polymer should have enough affinity for the magnetic nanoparticles present at the surface of the fluorescent core in order to coat the nanoassembly, while avoiding to take off part of the magnetic shell.

The presence of the polymer should not induce the aggregation of the nanoassemblies both during manufacturing and during use in biological media.

The polymer should be functionalizable, preferably the polymer should present a multiplicity of functionalizable patterns.

The polymer should present biocompatibility.

The Applicant evidenced that negatively charged polyelectrolytes meet above specifications. According to a specific embodiment of the invention, the preferred polymer is polyacrylic acid (PAA).

Advantageously, the mean size of the fluo@mag@polymer does increase in a reasonable range compared to that of the uncoated fluo@mag nanoassembly, keeping the adequate dimensions for applications in vivo.

SUMMARY

The present invention relates to a nanoassembly comprising:

a fluorescent core comprising fluorescent organic molecules, and magnetic nanoparticles contacting the surface of said fluorescent core.

According to one embodiment, the fluorescent organic molecules are compounds of Formula I, $$\text{[Structure of Formula I]}$$

wherein:

X represents O or $CH_2$;

n represents an integer selected from 1, 2, 3 and 4;

$R^1$ represents $-CO_2H$ or $-P(O)(OH)_2$;

$R^2, R^3, R^4, R^5, R^6$ and $R^7$ represent each independently an optionally functionalized group selected from alkyl and ester or polyethylene glycol, preferably $R^2, R^3, R^4, R^5, R^6$ and $R^7$ represent each a methyl group.

According to one embodiment, the magnetic nanoparticles are superparamagnetic nanoparticles selected from the group comprising $\gamma$-$Fe_2O_3$ and $Fe_3O_4$.

According to one embodiment, the nanoassembly of the invention has a hydrodynamic diameter ranging from 20 to 700 nm.

According to one embodiment, the fluorescent core comprises a number of organic fluorescent molecule ranging from $1\times10^4$ to $1\times10^7$. According to one embodiment, the nanoassembly comprises a number of magnetic nanoparticles ranging from $1\times10^2$ to $1\times10^6$.

According to one embodiment, the nanoassembly of the invention further comprises at least one polymer. According to one embodiment, the polymer is an ionic polymer, preferably a polyelectrolyte.

According to one embodiment, the polymer is of Formula II, $$H-P-\left[\left(CH_2-CH\right)_x^X-co-\left(CH_2-CH\right)_y^Y-co-\left(CH_2-C\begin{smallmatrix}Z\\|\\H\end{smallmatrix}\right)_z\right]_m-H$$

wherein, m represents a positive integer ranging from 20 to 150;

x, y and z represent each independently a percentage of m, ranging from 0% to 100% of m, wherein x+y+z is equal to 100% of m;

X represents $-COOH$, alkyl, aryl; Y represents $-(C=O)-O-L^1-R^8$, $-(C=O)-S-L^1-R^8$, $-(C=O)-NH(-L^1-R^8)$ or $-(C=S)-NH(-L^1-R^8)$ wherein $L^1$ represents a spacer selected from alkyl, alkene, aryl, arylalkyl, polyethylene glycol or polypropylene glycol linking groups having 1 to 150 chain atoms, wherein the linking group can be optionally interrupted or terminated by one or more $-O-$, $-S-$, $-NR^9-$, $-CO-$, $-NHCO-$, $-CONH-$ or a combination thereof, wherein $R^9$ is H or alkyl;

$R^8$ represents a reactive group selected from $N_3$, amino, alkylamino, COOH, amide, maleimide, alkyne, SH, OH, ester, activated ester, activated carboxylic acid, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, acetylene, olefins, polyenes, alkylacrylates, oxetane, ammoniums, oxoniums, phosphoniums, sulfoniums, positively charged metal complexes;

Z represents $-(C=O)-O-L^2-R^{10}$, $-(C=O)-S-L^2-R^{10}$, $-(C=O)-NH(-L^2-R^{10})$ or $-(C=S)-NH(-L^2-R^{10})$ wherein L² represents a single bond or a spacer selected from alkyl, alkene, aryl, arylalkyl, polyethylene glycol or polypropylene glycol linking groups having 1 to 150 chain atoms, wherein the linking group can be optionally interrupted or terminated by one or more —O—, —S—, —NR⁹—, —CO—, —NHCO—, —CONH— or a combination thereof, wherein $R^9$ is H or alkyl; optionally additionally comprising a residue of a reactive group through which $L^2$ is bonded to $R^{10}$;

$R^{10}$ represents a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, ligand, substrate, biotin, avidin, synthetic polymer, polyethylene glycol, polypropylene glycol, polymeric microparticle, nanoparticle, fluorophore, chromophore, radioisotope, macrocyclic complexes of radioisotope, and combinations thereof.

According to one embodiment, the polymer is polyacrylic acid.

According to one embodiment, the nanoassembly comprising a polymer has a hydrodynamic diameter ranging from 50 to 800 nm.

The invention also relates to a pharmaceutical composition comprising the nanoassembly of the invention, in combination with at least one pharmaceutically acceptable vehicle.

The invention further relates to a medicament comprising the nanoassembly according to the invention.

The invention also relates to the use of the nanoassembly of the invention, for bimodal magnetic and fluorescent imaging. The invention also relates to the use of the nanoassembly of the invention, for cell sorting.

DEFINITIONS

In the present invention, the following terms have the following meanings:

"nanoassembly" refers to a nanometer-sized architecture wherein at least one dimension is lower than 700 nm, featuring the tight arrangement of nanoparticles. According to a preferred embodiment, the nanoassembly of the invention is of spherical shape.

"fluorescent" refers to an emissive property following light excitation upon one- or two-photon excitation in the UV-visible or near infrared (up to 900 nm) range.

"magnetic" refers to the ability to respond to an applied external magnetic field upon alignment of magnetic dipoles along the direction of the magnetic field.

"superparamagnetic" refers to the magnetic property encountered for nanoparticles smaller than a single magnetic monodomain. Such nanoparticles steadily orient upon applying an external magnetic field until a maximum value of the global magnetization, dubbed saturation magnetization, is reached. They relax when removing the magnetic field, with no magnetic hysteresis (no remanence) at room temperature. In the absence of an external magnetic field, superparamagnetic nanoparticles exhibit non-permanent magnetic moment due to thermal fluctuations of the dipole orientation (Neel relaxation) and nanoparticle position (Brownian relaxation).

"hydrodynamic diameter" refers to the diameter of nanoparticles in solution, as measured by dynamic light scattering, taking into account the extension of the first solvation shell around the nanoparticles.

"polyelectrolyte" refers to a water-soluble macromolecule displaying a multiplicity of ionizable or ionic repeating units and able to electrostatically interact with the polarized surface of metal oxide materials, especially iron oxide nanoparticles.

"alkyl" refers to any saturated linear, branched or cyclic hydrocarbon chain, with 1 to 50 carbon atoms, preferably 1 to 6 carbon atoms. Suitable alkyl groups include methyl, ethyl, propyl (n-propyl, i-propyl, n-butyl), butyl (i-butyl, s-butyl and t-butyl), pentyl and its isomers (e.g. n-pentyl, iso-pentyl), and hexyl and its isomers (e.g. n-hexyl, iso-hexyl). The alkyl group may be substituted or comprise heteroatoms.

"alkene" refers to any linear or branched hydrocarbon chain having at least one carbon-carbon double bond, of 2 to 50 carbon atoms, and preferably 2 to 6 carbon atoms. The alkenyl group may be substituted. Examples of alkenyl groups are ethenyl, propen-2-yl, buten-2-yl, buten-3-yl, penten-2-yl and its isomers, hexen-2-yl and its isomers, pentadi-2,4-enyl and the like. The alkenyl group may be substituted by a saturated or unsaturated aryl group.

"alkyne" refers to any linear or branched hydrocarbon chain having at least one carbon-carbon triple bond, of 2 to 50 carbon atoms, and preferably 2 to 6 carbon atoms. Non limiting examples of alkynyl groups are ethynyl, propyn-2-yl, butyn-2-yl, 3-butyn-3-yl, pentyn-2-yl and its isomers, hexyn-2-yl and its isomers- and the like.

"aryl" refers to a aromatic hydrocarbon group having a single ring (i.e. phenyl) or multiple aromatic rings fused together (e.g. naphtyl) or linked covalently, typically containing 5 to 20 atoms; preferably 6 to 12, wherein at least one ring is aromatic. The aromatic ring may optionally be fused to one to two additional rings (either cycloalkyl, heterocyclyl or heteroaryl). Non-limiting examples of aryl comprise phenyl group, the biphenyl group, the 1-naphthyl group, the 2-naphthyl group, the tetrahydronaphthyl group, the indanyl group, the binaphthyl group, the fluorenyl group and the anthracenyl group.

"arylalkyl" refers to an alkyl group substituted by an aryl group, such as for example the phenyl-methyl group.

"activated ester" refers for example to N-hydroxysuccinimide ester, N-hydroxyglutarimide ester, N-hydroxybenzotriazole ester or maleimide ester.

"activated carboxylic acid" refers for example to acid anhydride or acid halide.

DETAILED DESCRIPTION

A. Nanoassemblies

A.1. Fluo@Mag Nanoassemblies: Fluorescent Core and Magnetic Nanoparticles

The present invention relates to magnetic and fluorescent nanoassemblies (fluo@mag nanoassembly). Especially, the nanoassembly of the invention comprises a fluorescent core, preferably an organic fluorescent core, surrounded by magnetic nanoparticles contacting the surface of the fluorescent core, preferably superparamagnetic nanoparticles.

According to one embodiment, the nanoassembly of the invention comprises a fluorescent core comprising fluorescent organic molecules, and magnetic nanoparticles contacting the surface of said fluorescent core.

According to a preferred embodiment, the nanoassembly of the invention comprises
a fluorescent core comprising fluorescent organic molecules, and
superparamagnetic nanoparticles contacting the surface of said fluorescent core.

FIG. 1 illustrates the reverse architecture of the fluo@mag nanoassembly of the invention.

In the nanoassembly of the invention, the fluorescent core and the magnetic nanoparticles are not linked by covalent bonds.

Fluorescent Core

According to one embodiment, the fluorescent core of the nanoassembly is an organic fluorescent core. Preferably, the fluorescent core is "matrix-free", i.e. does not comprise a matrix, wherein the matrix may be for example silica, oil droplets and vesicles, polymer, liquid crystal micelles, liposomes, nanocapsules, gelatin nanoparticles. In other words, the fluorescent core of the invention is not a matrix wherein fluorescent organic molecules are encapsulated or embedded.

According to one embodiment, the fluorescent core of the nanoassembly of the invention comprises fluorescent organic molecules.

Preferably, the fluorescent core is of spherical shape.

The fluorescent core presents the advantage to have a high density of fluorescent molecules and weak emission quenching in the solid-state.

The fluorescent core may be obtained by a simple manufacturing process. According to one embodiment, the fluorescent core may be obtained following a one-step nucleation process.

According to one embodiment, the fluorescent organic molecules of the fluorescent core are those described in Faucon et al. *J. Mater. Chem. C*, 2013, 1 (24), 3879-3886.

According to one embodiment, the fluorescent organic molecules of the fluorescent core are compounds of Formula I:

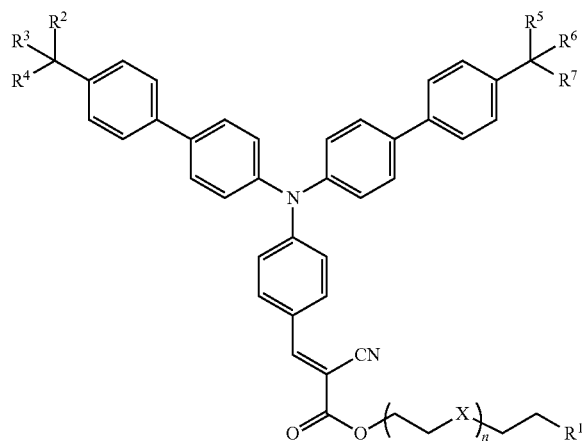

wherein:
X represents O or $CH_2$;
n is an integer selected from 1, 2, 3 and 4;
$R^1$ represents $-CO_2H$ or $-P(O)(OH)_2$;
$R^2$, $R^3$, $R^4$, $R^5$, $R^6$ and $R^7$ represent each independently an optionally functionalized group selected from alkyl and ester or polyethylene glycol, preferably $R^2$, $R^3$, $R^4$, $R^5$, $R^6$ and $R^7$ represent each a methyl group.

According to a specific embodiment of the invention, the fluorescent organic molecules of the fluorescent core are of Formula (Ia) or (Ib):

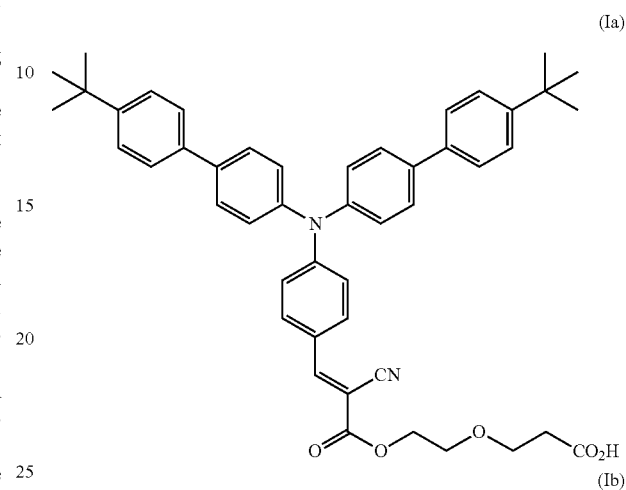

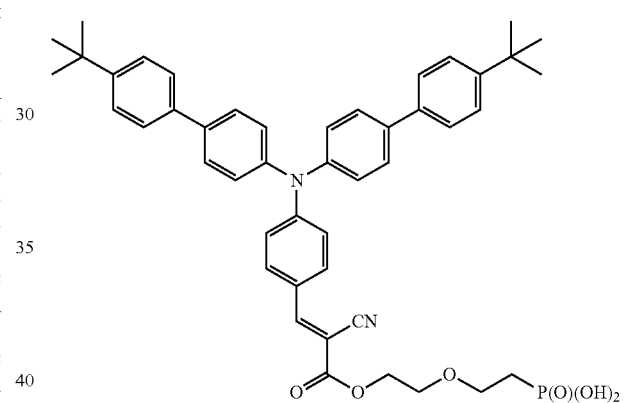

In one embodiment, the absorption wavelength of the fluorescent core is ranging from 200 to 800 nm, preferably from 300 to 650 nm, more preferably from 400 to 500 nm.

In one embodiment, the emission wavelength of the fluorescent core is ranging from 300 to 1000 nm, preferably from 400 to 800 nm, more preferably from 550 to 700 nm.

According to one embodiment, the fluorescent core comprises a number of organic fluorescent molecules ranging from $1 \times 10^4$ to $1 \times 10^7$, preferably from $1 \times 10^4$ to $1 \times 10^6$, more preferably from $1 \times 10^5$ to $1 \times 10^6$.

In one embodiment, the fluorescent organic molecule comprises an ionizable group, preferably an anionic group, which is able to complex magnetic nanoparticles.

According to one embodiment, the fluorescent core further comprises active agents such as for example therapeutically active agents.

Magnetic Nanoparticles

According to a preferred embodiment, the magnetic nanoparticles of the nanoassemblies of the invention are superparamagnetic nanoparticles. Superparamagnetic particles become magnetized up to their saturation magnetization by applying an external magnetic field, while they do not possess any residual magnetization at room temperature when the magnetic field is removed.

According to one embodiment, the magnetic nanoparticles are selected from the group comprising $\gamma\text{-Fe}_2\text{O}_3$, $\text{Fe}_3\text{O}_4$, $\text{CoFe}_2\text{O}_4$, $\text{MnFe}_2\text{O}_4$, $\text{CuFe}_2\text{O}_4$, $\text{NiFe}_2\text{O}_4$. Preferably, magnetic nanoparticles are nanoparticles of maghemite iron oxide $\gamma\text{-Fe}_2\text{O}_3$ or magnetite $\text{Fe}_3\text{O}_4$.

According to one embodiment, the nanoassembly of the invention comprises a number of magnetic nanoparticles ranging from $1\times10^2$ to $1\times10^6$, preferably from $1\times10^3$ to $1\times10^5$, more preferably from $0.5\times10^4$ to $5\times10^4$.

Advantageously, the magnetic nanoparticles are superparamagnetic and possess enhanced relaxivity properties upon tight association at the surface of the fluorescent core compared to those of free nanoparticles.

According to one embodiment, the magnetic nanoparticles present saturation magnetization $M_S$ values ranging from 20 to 100 emu $g^{-1}$, preferably from 20 to 55 emu $g^{-1}$.

According to one embodiment, compared to free nanoparticles, the magnetic nanoparticles within the nanoassembly of the invention present R2/R1 ratio larger than 2, preferably larger than 4, more preferably larger than 6 at clinical MRI frequencies.

Advantageously, the magnetic nanoparticles present in the nanoassemblies of the invention exert cooperative effects, leading to an important improvement of the MRI (magnetic resonance imaging) contrast. Therefore, the nanoassemblies of the invention enable MRI imaging even at low iron concentrations.

Nanoassembly Properties

In a preferred embodiment, the fluorescent core of the nanoassembly of the invention comprises fluorescent organic molecules of Formula (Ia) and the magnetic nanoparticles are nanoparticles of $\gamma\text{-Fe}_2\text{O}_3$ or $\text{Fe}_3\text{O}_4$.

In a preferred embodiment, the fluorescent core of the nanoassembly of the invention comprises fluorescent organic molecules of Formula (Ib) and the magnetic nanoparticles are nanoparticles of $\gamma\text{-Fe}_2\text{O}_3$ or $\text{Fe}_3\text{O}_4$.

Advantageously, the fluorescent organic molecules and the magnetic nanoparticles comprised in the nanoassembly of the invention are such that the emission wavelength of the fluorescent core is red-shifted compared to the absorption wavelength of the magnetic nanoparticles in order to avoid emission quenching upon inner-filter effect.

According to one embodiment, the fluorescent organic molecules have a Stokes shift higher than 4500 $cm^{-1}$.

In one embodiment of the invention, the hydrodynamic diameter of the nanoassembly is ranging from 20 to 800 nm, preferably from 50 to 500 nm, more preferably from 80 to 200 nm.

In a specific embodiment, when the nanoassembly comprises fluorescent organic molecules of Formula (Ia) and/or (Ib) and $\gamma\text{-Fe}_2\text{O}_3$ magnetic nanoparticles, the hydrodynamic diameter is preferably ranging from 80 to 200 nm.

In one embodiment, the nanoassemblies of the invention are stored in acidic media. In this case, anionic counterions enable the stabilization of the nanoassemblies through electrostatic repulsion, which avoids aggregation of the nanoassemblies.

A.2. Fluo@Mag@Polymer Nanoassemblies: Fluorescent Core, Magnetic Nanoparticles and Polymer The present invention further relates to a magnetic and fluorescent nanoassembly further comprising a discontinuous coating of polymers (fluo@mag@polymer nanoassembly). Especially, the nanoassemblies of the invention comprise a fluorescent core, preferably an organic fluorescent core, partially or totally surrounded by magnetic nanoparticles contacting the surface of the fluorescent core, preferably superparamagnetic nanoparticles, and further continuously or discontinuously coated by polymers.

Advantageously, the polymer replaces the anionic counterions used to stabilize the fluo@mag nanoassembly in acidic medium and thus allows for the stabilization of the nanoassembly in neutral medium. Advantageously, since the fluo@mag@polymer nanoassembly is stable in neutral medium, it can be used in biological medium.

In one embodiment, the fluo@ mag@ polymer nanoassembly of the invention is stable at a pH ranging from 3 to 12.

In one embodiment, the fluo@mag@polymer nanoassembly of the invention is stable at an ionic strength ranging from 0 to 1 mol/L of NaCl, preferably from 0.05 to 0.3 mol/L of NaCl.

According to one embodiment, the nanoassembly of the invention comprises:
 a fluorescent core, comprising fluorescent organic molecules;
 magnetic nanoparticles contacting the surface of the fluorescent core; and
 at least one polymer.

The polymer is preferably contacting the surface of the nanoassembly comprising a fluorescent core having at its surface magnetic nanoparticles. FIG. 2 illustrates the architecture of the fluo@ mag@ polymer nanoassembly of the invention.

According to one embodiment, the fluo@mag nanoassemblies of the invention further comprise at least one polymer at their surface, leading to fluo@mag@polymer nanoassemblies.

The fluo@mag@polymer nanoassemblies of the invention are advantageously hydrophilic, colloidally stable in acidic and alkaline media, photostable under irradiation, do not possess apparent cytotoxicity, present magnetic and fluorescence properties close or superior to those of the constitutive fluorescent core and magnetic nanoparticles, and do not deaggregate into their constitutive fluorescent and magnetic nanoparticles or molecules.

It was evidenced that the addition of the polymer protective shell leads to a minimal (namely about 40 nm) increase of the hydrodynamic diameter of the assembly only. In one embodiment, the fluo@mag@polymer nanoassembly has a hydrodynamic diameter ranging from 50 to 800 nm, preferably from 70 to 600 nm, more preferably from 90 to 300 nm.

The fluo@mag@polymer nanoassemblies may be stored after lyophilization. Re-dispersion after lyophilization may easily be achieved. According to one embodiment, re-dispersion after lyophilization is performed in a solvent selected from water, buffer, alcoholic solvents.

The fluo@mag@polymer nanoassemblies of the invention present the advantage not to aggregate when placed in a solvent.

The fluo@mag@polymer nanoassemblies of the invention present the advantage to be internalized in cells while not penetrating into the nucleus.

Polymer

In one embodiment, the polymer used to continuously or discontinuously coat the nanoassembly of the invention is an ionic polymer, preferably a polyelectrolyte.

According to one embodiment, the polymer comprises anionic functions able to interact with the magnetic particles of the nanoassemblies of the invention.

According to one embodiment, the polymer is not cross-linked.

According to one embodiment, the polymer is a "functionalizable polymer", i.e. the polymer comprises at least one reactive group. By "reactive group", it is herein referred to a group capable of reacting with another chemical group to form a covalent bond and/or an electrostatic bond, i.e. is covalently reactive and/or ionically reactive under suitable reaction conditions, and generally represents a point of attachment for another substance. The reactive group is a moiety on the polymer that is capable of chemically reacting with a functional group on a different compound to form a covalent linkage and/or an electrostatic linkage. Reactive groups generally include nucleophiles, electrophiles, dienophiles, dipolarophiles, cations and photoactivable groups.

When a reactive group is present on the polymer used in the nanoassembly of the invention, it is possible to functionalize the nanoassembly.

According to one embodiment, the polymer comprises at least one reactive group selected from the group comprising $N_3$, amino, alkylamino, COOH, amide, maleimide, alkyne, SH, OH, ester, activated ester, activated carboxylic acid, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, acetylene, olefins, polyenes, alkylacrylates, oxetane, ammoniums, oxoniums, phosphoniums, sulfoniums, positively charged metal complexes.

In one embodiment, the polymer comprises at least one lateral chain substituted by at least one reactive group.

According to another embodiment, the polymer is a "functionalized polymer", i.e. the polymer comprises at least one bioactive group. The bioactive group may enable to target the nanoassembly coated with the polymer by the recognition of biological targets. The bioactive group may also confer biological activity to the nanoassembly coated with the polymer.

According to one embodiment, the bioactive group is selected from amino acid, peptide, protein, antibody, enzyme, polysaccharide, dextran, benzylguanine, lipid, lipid assembly, fatty acid, nucleoside, nucleotide, oligonucleotide, hapten, aptamer, ligand, substrate, biotin, avidin, synthetic polymer, polyethylene glycol, polypropylene glycol, polymeric microparticle, nanoparticle, fluorophore, chromophore, radioisotope, macrocyclic complexes of radioisotope, and combinations thereof.

The bioactive group may also impart the polymer-coated nanoassembly with furtivity. In this way, clearance of the nanoassembly from the bloodstream by the mononuclear phagocyte system (reticuloendothelial system) is impaired and longer circulation times in the body are obtained. In this case, the bioactive group preferably comprises or consists in a PEG moiety.

According to one embodiment, the bioactive group is directly present on the polymer. Alternatively, the bioactive group is introduced on the polymer through reaction with a reactive group. Especially, the bioactive group may be introduced on the polymer by peptide coupling or by click chemistry.

Optionally, a spacer may be present between the polymer and the bioactive group.

In one embodiment, the bioactive group is present on a lateral chain of the polymer. According to another embodiment, the bioactive group is present at one extremity of the polymer or at both extremities.

Advantageously, the functionalization of the polymer by bioactive groups occurs without any loss of the biological properties of said bioactive groups.

In one embodiment, the polymer, and especially the "functionalizable polymer", has a molecular weight ranging from 1 to 10 kDa, preferably from 1 to 5 kDa. The "functionalized polymer" may have a molecular weight greater than 10 kDa, depending on the nature of the bioactive group used for functionalization.

Commonly used nomenclature for a copolymer comprising a total of m monomers, x % of said monomers being monomer A, y % of said monomers being monomer B and z % of said monomers being monomer C is: $P[A_x\text{-co-}B_y\text{-co-}C_z]_m$. When the extremities of the copolymer are specific, they may be indicated on either side of $P[A_x\text{-co-}B_y\text{-co-}C_z]_m$, namely under the form: $R^1-P[A_x\text{-co-}B_y\text{-co-}C_z]_m-R^2$. This nomenclature is used hereafter.

In a specific embodiment, the polymer is polyacrylic acid or a derivative thereof of formula II:

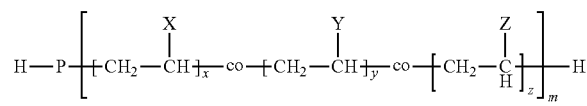

wherein, m represents a positive integer ranging from 20 to 150;

x, y and z represent each independently a percentage of m, ranging from 0% to 100% of m, wherein x+y+z is equal to 100% of m;

X represents —COOH, alkyl, aryl; Y represents —(C=O)—O-$L^1$-$R^8$, —(C=O)—S-$L^1$-$R^8$, —(C=O)—NH(-$L^1$-$R^8$) or —(C=S)—NH(-$L^1$-$R^8$) wherein $L^1$ represents a spacer selected from alkyl, alkene, aryl, arylalkyl, polyethylene glycol or polypropylene glycol linking groups having 1 to 150 chain atoms, wherein the linking group can be optionally interrupted or terminated by one or more —O—, —S—, —$NR^9$—, —CO—, —NHCO—, —CONH— or a combination thereof, wherein $R^9$ is H or alkyl;

$R^8$ represents a reactive group selected from $N_3$, amino, alkylamino, COOH, amide, maleimide, alkyne, SH, OH, ester, activated ester, activated carboxylic acid, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, acetylene, olefins, polyenes, alkylacrylates, oxetane, ammoniums, oxoniums, phosphoniums, sulfoniums, positively charged metal complexes;

Z represents —(C=O)—O-$L^2$-$R^{10}$, —(C=O)—S-$L^2$-$R^{10}$, —(C=O)—NH(-$L^2$-$R^{10}$) or —(C=S)—NH(-$L^2$-$R^{10}$) wherein L² represents a single bond or a spacer selected from alkyl, alkene, aryl, arylalkyl, polyethylene glycol or polypropylene glycol linking groups having 1 to 150 chain atoms, wherein the linking group can be optionally interrupted or terminated by one or more —O—, —S—, —NR⁹—, —CO—, —NHCO—, —CONH— or a combination thereof, wherein R⁹ is H or alkyl; optionally additionally comprising a residue of a reactive group through which L² is bonded to R¹⁰;

R¹⁰ represents a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, ligand, substrate, biotin, avidin, synthetic polymer, polyethylene glycol, polypropylene glycol, polymeric microparticle, nanoparticle, fluorophore, chromophore, radioisotope, macrocyclic complexes of radioisotope, and combinations thereof.

x+y+z is equal to 100% of m, at least one of x, y or z may be equal to 0% of m. According to one embodiment, the polymer of formula II is of formula II':

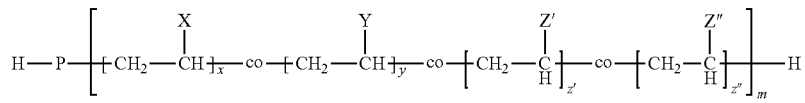

wherein, m, X and Y are as defined in formula II;

x, y, z' and z'' represent each independently a percentage of m, ranging from 0% to 100% of m, wherein x+y+z'+z'' is equal to 100% of m;

Z' and Z'' represent each independently —(C=O)—O-L²-R¹⁰, —(C=O)—S-L²-R¹⁰, —(C=O)—NH(-L²-R¹⁰) or —(C=S)—NH(-L²-R¹⁰) wherein L² represents a single bond or a spacer selected from alkyl, alkene, aryl, arylalkyl, polyethylene glycol or polypropylene glycol linking groups having 1 to 150 chain atoms, wherein the linking group can be optionally interrupted or terminated by one or more —O—, —S—, —NR⁹—, —CO—, —NHCO—, —CONH— or a combination thereof, wherein R⁹ is H or alkyl; optionally additionally comprising a residue of a reactive group through which L² is bonded to R¹⁰;

R¹⁰ represents a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, ligand, substrate, biotin, avidin, synthetic polymer, polyethylene glycol, polypropylene glycol, polymeric microparticle, nanoparticle, fluorophore, chromophore, radioisotope, macrocyclic complexes of radioisotope, and combinations thereof.

According to one embodiment, one of Z' and Z'' represents —(C=O)—O-L²-R¹⁰, —(C=O)—S-L²-R¹⁰, —(C=O)—NH(-L²-R¹⁰) or —(C=S)—NH(-L²-R¹⁰), wherein L² is a single bond and R¹⁰ is a polyethylene glycol chain.

According to one embodiment, one of Z' and Z'' represents —(C=O)—O-L²-R¹⁰, —(C=O)—S-L²-R¹⁰, —(C=O)—NH(-L²-R¹⁰) or —(C=S)—NH(-L²-R¹⁰), wherein L² is a polyethylene glycol chain and R¹⁰ is a bioactive group different from a polyethylene glycol chain.

According to one embodiment, Z' represents —(C=O)—O-L²-R¹⁰, —(C=O)—S-L²-R¹⁰, —(C=O)—NH(-L²-R¹⁰) or —(C=S)—NH(-L²-R¹⁰), wherein L² is a single bond and R¹⁰ is a polyethylene glycol group; and Z'' represents —(C=O)—O-L²-R¹⁰, —(C=O)—S-L²-R¹⁰, —(C=O)—NH(-L²-R¹⁰) or —(C=S)—NH(-L²-R¹⁰), wherein L² is a polyethylene glycol chain and R¹⁰ is a bioactive group different from a polyethylene glycol chain.

According to an embodiment, the polymer is random, alternate or block copolymer. In another embodiment, the ligand is a statistic copolymer. In another embodiment, said ligand is a random or block copolymer.

B. Process for Manufacturing the Nanoassemblies of the Invention

B.1. Manufacturing of Fluo@Mag Nanoassemblies

The present invention further relates to a process for the manufacturing of the nanoassemblies of the invention. Especially, the invention relates to the process for manufacturing the fluo@ mag nanoassemblies of the invention.

According to one embodiment, the process of the invention comprises injecting a solution of fluorescent organic molecules into a dispersion of magnetic nanoparticles under stirring.

According to one embodiment, the solution of fluorescent organic molecules comprises an amount of fluorescent organic molecules ranging from 0.005 to 1% in weight relative to the total weight of the solution, preferably from 0.01 to 1% w/w, more preferably from 0.05 to 1% w/w.

According to one embodiment, the solvent of the solution of fluorescent organic molecules is an organic solvent, preferably an organic solvent miscible with water, preferably THF.

According to one embodiment, the dispersion of magnetic nanoparticles comprises an amount of magnetic nanoparticles ranging from 0.001 to 0.1% in weight relative to the total weight of the solution, preferably from 0.002 to 0.05% w/w, more preferably from 0.004 to 0.01%.

According to one embodiment, the solvent of the dispersion of magnetic nanoparticles is an aqueous solvent, preferably water.

Preferably, the stiffing during the manufacturing process is performed by means of a vortex.

B.2. Manufacturing of Fluo@Mag@Polymer Nanoassemblies

The present invention further relates to a process for the manufacturing of the fluo@mag@polymer nanoassemblies of the invention.

According to one embodiment, the process of manufacturing of the fluo@mag@polymer nanoassemblies comprises the manufacturing process of fluo@mag nanoassemblies as described above and a subsequent step of addition of a solution of polymer.

According to one embodiment, the process of manufacturing of the fluo@mag@polymer nanoassemblies comprises:

injecting a solution of fluorescent organic molecules into a dispersion of magnetic nanoparticles under stirring, to form fluo@ mag nanoassemblies; and adding the polymer.

According to one embodiment, the polymer is added under the form of a solid, preferably under the form of a powder. In an alternative embodiment, the polymer is added in solution, preferably an aqueous solution.

According to a preferred embodiment, the process further comprises a subsequent step of pH adjustment, preferably to a pH ranging from 6 to 12, preferably about pH 8. Preferably, pH adjustment is performed by the dropwise addition of a base, said base being preferably ammonium hydroxide, preferably the base is ammonium hydroxide at 1 mol·$L^{-1}$.

According to a preferred embodiment, the process further comprises a subsequent step of dialysis, preferably a subsequent step of dialysis against Millipore water. Such a dialysis may enable to reach a pH of about 7.

The process may further comprise a step of lyophilization. Lyophilized nanoassemblies are easily stored for a prolonged period of time.

B.3. Functionalization of Fluo@Mag@Polymer Nanoassemblies

According to one embodiment, the polymer used to form the fluo@mag@polymer nanoassemblies of the invention is a functionalized polymer. In this case, the formation of the fluo@mag@polymer nanoassemblies leads to functionalized fluo@mag@polymer nanoassemblies.

According to another embodiment, the polymer used to form the fluo@mag@polymer nanoassemblies of the invention is a functionalizable polymer. In this case, functionalization of the fluo@mag @polymer nanoassemblies may be performed after formation of the fluo@mag@polymer nanoassemblies by reacting the reacting groups of the polymer with a bioactive agent comprising a suitable reactive group. For example, when the polymer comprises carboxylic functions, the nanoassemblies may be functionalized after formation by reaction with a bioactive agent comprising an amine function through amide bond formation.

C. Use of the Nanoassemblies of the Invention

The present invention further relates to the use of the nanoassemblies of the invention.

Imaging

According to one embodiment, the nanoassemblies of the invention may be used for imaging. Preferably, the nanoassemblies of the invention are used for bimodal imaging, namely for fluorescence imaging and magnetic resonance imaging.

In one embodiment, imaging using the nanoassemblies of the invention may be performed in vivo. In another embodiment, imaging using the nanoassemblies of the invention may be performed in vitro.

The invention further relates to a method of medical imaging which comprises administering to a patient in need thereof the nanoassemblies according to the invention and recording fluorescence and magnetic signals.

According to one embodiment, the nanoassemblies of the invention may be used for diagnosis purposes.

According to one embodiment, the nanoassemblies of the invention may be used for assessing, in vitro or in vivo, the biodistribution of substances of interest.

Therapy

According to one embodiment, the nanoassemblies of the invention may be used for therapy.

According to one embodiment, the nanoassemblies of the invention may comprise a therapeutically active agent. In this case, the nanoassemblies may act as a delivery means of said active agent.

Magnetic properties of the nanoassemblies of the invention may be used to generate hyperthermia. Therefore, the nanoassemblies of the invention may be used to treat diseases by hyperthermia. Especially, hyperthermia may be used to destroy tumors.

In the case of nanoassemblies bearing a polymer protective shell, the polymer may be functionalized by targeting agents and/or pharmaceutically active agents.

The present invention relates to a pharmaceutical composition comprising a nanoassembly according to the invention, optionally functionalized with a pharmaceutically active agent, in combination with at least one pharmaceutically acceptable vehicle.

The invention also relates to a medicament comprising a nanoassembly according to the invention, said nanoassembly being optionally functionalized with a pharmaceutically active agent.

The invention also relates to the use of a nanoassembly according to the invention for the manufacture of a medicament, preferably for the treatment of and/or prevention of cancer.

According to one embodiment, the nanoassembly of the invention is for use in the treatment and/or prevention of cancer.

According to one embodiment, the nanoassembly of the invention, preferably the functionalized nanoassembly of the invention, is for use as an active therapeutic substance.

Cell Sorting

The present invention further relates to the use of the nanoassembly of the invention for cell sorting, involving magnetic and/or fluorescent properties of the nanoassemblies of the invention.

Especially, fluorescent properties may be used to sort cells by flow cytometry. Flow cytometry methods are known by those skilled in the art.

Magnetic properties of the nanoassemblies of the invention may also be used for magnetic cell sorting.

According to one embodiment, the nanoassemblies of the invention are used for fluorescent cell sorting. According to another embodiment, the nanoassemblies of the invention are used for magnetic cell sorting. According to one embodiment, the nanoassemblies of the invention are used for fluorescent and magnetic cell sorting.

EXAMPLES

Figure 1:
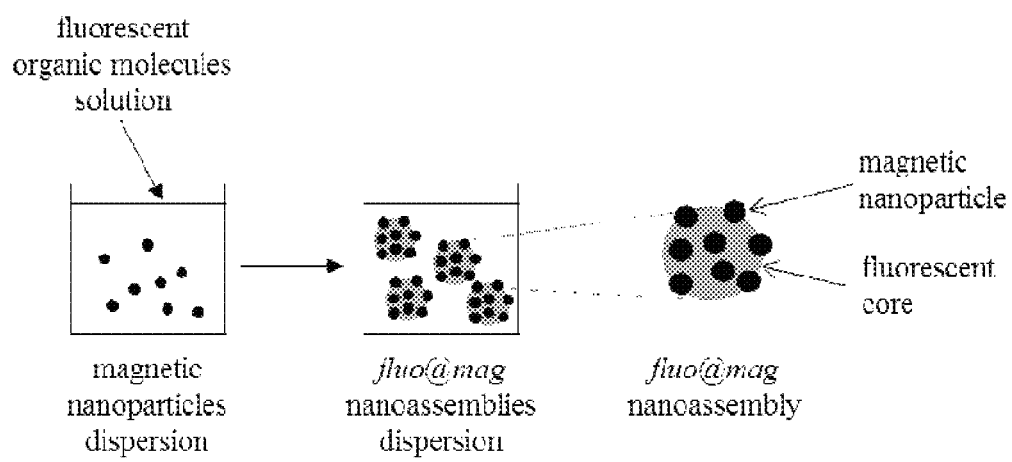
FIG. 1 is a schematic representation of the fluo@mag nanoassemblies of the invention and of their process of manufacturing.
Figure 2:
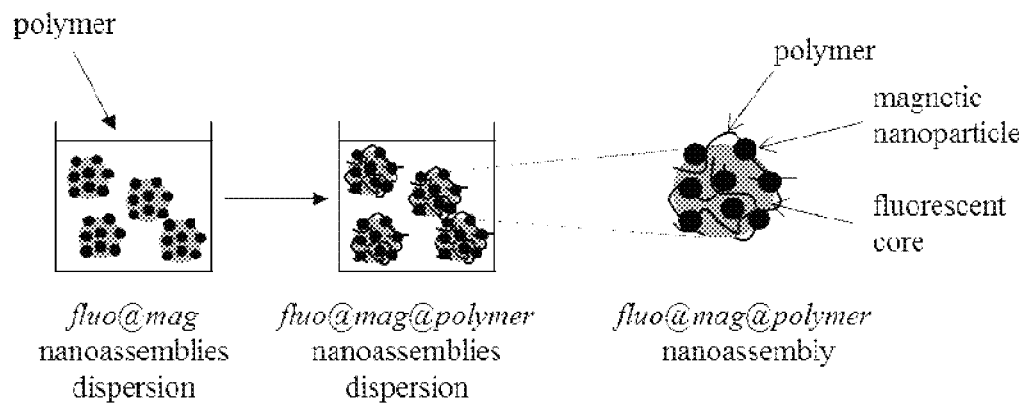
FIG. 2 is a schematic representation of the fluo@mag@polymer nanoassemblies of the invention and of their process of manufacturing.

The present invention is further illustrated by the following examples.

Material

All chemical reagents and solvents were purchased from commercial sources (Aldrich, Acros, SDS) and used as received. Spectroscopic grade solvents purchased from Aldrich were used for spectroscopic measurements.

ABBREVIATIONS

° C. Celsius degree
cm centimeter
DAPI 4',6'-diamidino-2-phenylindole
$D_H$ Hydrodynamic diameter
DLS Dynamic Light Scattering
DMEM Dulbecco/Vogt modified Eagle's minimal essential medium
DMSO Dimethylsulfoxide
emu 1 emu=$10^{-3}$ A m$^{-2}$=$10^{-3}$ J T$^{-1}$ features the unit of the magnetic moment
ENH Contrast magnetic resonance enhancement
G Gauss
h hour
HBSS Hank's Balanced Salt Solution
HEK Human Embryonic Kidney cell
K Kelvin
Kg kilogram
$\lambda$ Wavelength
LSM Laser Scanning Microscope
M mole per liter
MDa Mega Dalton
MDA Cell derived from metastatic site in human mammary gland/breast
MHz Mega Hertz
min minute
mL milliliter
MRI Magnetic Resonance Imaging
Ms saturation magnetization
MTT 3-(4,5-dimethylthiazol-2-yl)-2,5-diphenyltetrazolium bromide
ms millisecond
nm nanometer
NMR Nuclear Magnetic Resonance
NPs Nanoparticles
OCT Embedding matrix for cryotomy
PAA Polyacrylic acid
PBS phosphate buffered saline
R1 longitudinal relaxivity
R2 transverse relaxivity
RPMI Roswell Park Memorial Institute medium
s second
T Tesla
T1 Longitudinal relaxation time
T2 Transverse relaxation time
TE echo time
TEM Transmission Electron Microscopy
THF Tetrahydrofuran
TR repetition time
µM micromole per liter
UV ultraviolet
$\nu$ frequency Part A—Magnetic-Fluorescent Nanoasemblies 1. Synthetic Procedures 1.1 Fluorescent Organic Molecules Fluorescent molecules (Ia) and (Ib) were obtained as described in Faucon et al., *J. Mater. Chem. C.*, 2013, 1, 3879-3886.

Stock solutions of the fluorescent molecules (Ia) and (Ib) in spectrophotometric grade THF were prepared at concentrations ranging from 0.05 to 1 wt %.

1.2. Magnetic Nanoparticles

Nitrate-Stabilized Magnetic Nanoparticles.

Maghemite $\gamma$-Fe$_3$O$_3$ nanoparticles were prepared according to a procedure described by Massart et al (*IEEE Trans. Magn.*, 1981, 17, 1247-1248). Briefly, Fe(II) and Fe(III) salts were mixed in dilute hydrochloric acid. Quick alkalinization of the medium by adding concentrated ammonia enables the coprecipitation of magnetite Fe$_3$O$_4$ nanoparticles which were separated. The acidification of $\gamma$-Fe$_3$O$_4$ with nitric acid, followed by chemical oxidation with ferric nitrate at 80° C., yielded $\gamma$-Fe$_3$O$_3$ nanoparticles. After magnetic decantation, the red precipitate was dispersed in nitric acid (pH=1.2) since nitrate ions act as stabilizing counterions of the positively charged surface of the colloidal dispersion ($\zeta$=+25 mV).

1.3. Fluo@Mag Nanoassemblies Formation

A 0.1 wt % stock solution of fluorescent molecules in THF (50 µL) was injected into a 0.006 wt % solution of maghemite nanoparticles (2.5 mL) stirred by means of a vortex. When a nitric acid solution of magnetic nanoparticles was used, formation of hybrid nanoparticles, dubbed fluo@mag and comprising fluorescent molecules and iron oxide nanoparticles, is instantaneous.

2. Physico-Chemical Characterizations
2.1. Nanoassembly Characterizations
Methods The hydrodynamic diameter and size distribution of the nanoassemblies were determined by dynamic light scattering (DLS) by means of a nanoparticle size analyzer Zetasizer Nano ZS ZEN 3600 (Malvern Instruments) equipped with a 4 mW He—Ne laser, operating at 633 nm, and a photomultiplier detector collecting back-scattered light at an angle of 175°. Measurements were carried out at 20° C. on aqueous solutions of nanoassemblies. For each sample, intensity measurements were carried out in a multi-acquisition mode implying automatically adjusted correlograms, and averaged measurements on 3 acquisitions. Nanoparticle mean sizes and distribution widths were obtained by fitting each correlogram with a Cumulants algorithm.

Measurements of surface potential $\zeta$ were carried out by means of a Zetasizer Nano ZS ZEN 3600 (Malvern). The samples were placed in plastic cells. Several measurements were realized for each sample according to a predefined operating procedure.

The nanoassembly morphology was investigated by transmission electron microscopy (TEM, Hitachi HF2000-FEG). Solutions of nanoassemblies were deposited onto holey carbon coated copper grids (300 mesh) for all compounds except for the fluo@mag nanoparticles prepared from naked $\gamma$-$Fe_2O_3$ nanoparticles dispersed in dilute nitric acid, which were deposited onto holey carbon-coated gold grids (300 mesh).

Results

DLS and TEM measurements of fluo@mag nanoassemblies invariably yielded a mean diameter of 90-100 nm with a quite narrow size distribution. The nanoassemblies were colloidally stable in dilute nitric acid over months due to the negatively charged surface ($\zeta$=−33 mV) as measured by zetametry. TEM imaging revealed a raspberry-like assembly where $\gamma$-$Fe_2O_3$ nanoparticles contacted an organic nanosphere resulting from the self-aggregation of fluorescent molecules upon phase separation in aqueous solution.

2.2. Photophysical Measurements
Methods

UV-visible absorption spectra were recorded using a Varian Model Cary 5E spectrophotometer, using an integrating sphere DRA 2500. Corrected emission spectra were obtained using Jobin-Yvon. Inc spectrofluorimeter (Fluorolog 2). Fluorescence quantum yields $\Phi_f$ in solution were determined from Coumarine 540 A in EtOH ($\Phi_f$=0.38). Fluorescence intensity decays were measured at 580 nm using a monochromator (Hamamatsu MCP R3809U photomultiplier) by the time-correlated single-photon counting method (TCSPC) with a femtosecond laser excitation at 450 nm provided by a Spectra-Physics setup (Titanium-Sapphire Tsunami laser pumped by a doubled YAG laser (Millennia), pumped itself by a two-laser diode array, and doubling LBO crystals). Light pulses at 900 nm were selected by optoacoustic crystals at a repetition rate of 4 MHz, and then doubled at 450 nm.

Results

TABLE 1

Photophysical characteristics of fluo@mag nanoassemblies dispersed in water.

| $\lambda_{max}$(abs) [nm] | $\lambda_{max}$(em) [nm] | $\tau_1(f_1)$[1] [ns] | $<\tau_s>$[2] [ns] |
|---|---|---|---|
| 443 | 604 | 0.77 (34%), 0.24 (48%), 0.08 (14%), 0.04 (4%) | 0.39 |

[1]After laser excitation at 450 nm and detection at 580 nm.
[2]The intensity averaged time constant $<\tau_s>$ and normalized time fractional amplitude $f_i$ are calculated from global analysis using a multiexponential fit $I(t) = \sum_i [a_i \exp(-t/\tau_i)]$ with $a_i$ pre-exponential factor. The intensity-averaged time constant $<\tau_s>$ is defined as $(\tau_s) = \sum_i f_i \tau_i$ with $f_i = a_i \tau_i / \sum_j a_j \tau_j$.

The steady-state emission spectrum of the resulting fluo@mag nanoassemblies appeared very similar to that of fluorescent nanospheres in terms of energy (5 nm hypsochromic shift) and intensity ($\Phi_f$=0.01). Such a strong similarity stems from the main contribution of the fluorescent molecules comprised in the core, isolated from the interface. Partial emission quenching of the fluorescent nanospheres occurred via vibrational coupling between water and fluorescent molecules at the interface. For fluo@mag nanoassemblies, such quenching operates from electron transfer from the peripheral fluorescent molecules to the contacting iron oxide nanoparticles, which extends only to a few nanometers, with no effect on the fluorescent molecules inside the core. Shortening of the fluorescence decay was indeed observed by time-resolved fluorescence measurements. The longer lifetime constant, assessed at 1.49 ns for the fluorescent nanospheres, decreased to 0.08 ns for the fluo@mag nanoassemblies. These results emphasize the adopted approach of reverse architectures, insulating fluorescent molecules from iron oxide nanoparticles, known as strong emission quenchers.

2.3. Magnetic Measurements
Methods

Temperature dependent magnetization experiments on the colloidal suspension of fluo@mag nanoparticles ([Fe]~6.5×$10^{-5}$ mol·$L^{-1}$) were collected with a Quantum Design MPMS-5S SQUID magnetometer working at the temperature of 298 K and in the magnetic field range 0-2 T. The samples were diluted enough to avoid magnetic dipole-dipole interactions. The hysteresis loops were performed at 298 K in ZFC samples.

Results

The magnetization curve as a function of the applied magnetic field at 300 K shows very small coercivity, typical of superparamagnetic nanoparticles. The saturation magnetization values $M_S$ were found to be 22 emu·$g^{-1}$ for fluo@mag nanoassemblies. The reduced $M_S$ values relative to bulk maghemite (75-80 emu·$g^{-1}$) could be due to an increase in the surface anisotropy induced by chemisorption of the fluorescent molecules at the surface. Taking into account the iron mass determined from elemental analyses, fit of the magnetization curve provides a size distribution peaking at 7.29 nm (width $\sigma$=0.25) in fair agreement with the mean diameter of the initial nanoparticles ($D_H$=8.1 nm).

Such values tend to indicate that γ-Fe$_2$O$_3$ nanoparticles still keep their superparamagnetic behaviour when adsorbed.

Part B—Polymer Nanoassemblies

1. Synthetic Procedures

The protocols below describe the stabilization process of the fluorescent and magnetic fluo@mag nanoassemblies by using the PAA polyelectrolyte (M$_w$=2.1 kDa) as a polymer. Lyophilization of the stabilized fluo@mag@PAA nanoassemblies for biological uses in various media of interest is described.

Coating the fluo@mag nanoassemblies with an appropriate polyelectrolyte leads to stable colloidal solutions of nanoassemblies undergoing neither aggregation nor dissociation in aqueous media, which is suitable for in vitro and in vivo applications. Their subsequent lyophilization yields fine powders for a long-term storage which can be re-dispersed in media of various chemical natures and ionic strengths with no loss of the structural and functional properties.

1.1. Synthesis of Fluo@Mag@PAA Nanoassemblies

A solution of fluorescent compound (Ib) dissolved in THF (50 μL, 0.1 wt. %) was added under vigorous stirring to a solution of maghemite nanoparticles in nitric acid (2.5 mL, 0.006 wt. %, pH=1.2). After a few seconds, the magneto-fluorescent nanoassemblies (Ib)-fluo@mag were formed. Polyacrylic acid (2.1 kDa, 5 mg) was added as powder; ammonium hydroxide (1 mol·L$^{-1}$) was added dropwise under stirring until pH=9 was reached. The resulting translucent solution was allowed to stir for a further 30 min and dialyzed using a Spectra Por membrane (Standard Grade Regenerated Cellulose; cut-off: 8-10 kDa) against Millipore water (600 mL) over 24 h until the final pH solution of the fluo@mag@PAA nanoassemblies reaches a value of 7.

1.2. Lyophilization

In order to store the resulting fluo@mag@PAA nanoassemblies over a long period of time in the solid state, volumes (1 mL to 3 mL) of nanoparticle solutions were placed in glass vials such that the height of the liquid was not higher than 1 cm. The solution was allowed to freeze using liquid nitrogen. Lyophilization was performed over 9 h to 12 h to yield a dark red power that was stored at −18° C.

1.3. Re-Dispersion Procedures

Nanoassembly redispersion was easily performed by adding the adequate solvent (water, physiological media, alcoholic solvents such as ethanol) to the lyophilized sample. No ultrasound treatment was required since the nanoassemblies undergo no aggregation upon redispersion. Iron concentration in the range of 0.6-3×10$^{-3}$ mol·L$^{-1}$ could be obtained depending of the added amount of re-dispersing solvent.

2. Physico-Chemical Characterization

The characterizations of fluo@mag@PAA nanoassemblies in terms of size, surface potential, composition, photophysical and relaxivity properties are described. The stability of the colloidal suspensions as a function of time and the nature of solvent was checked by DLS, TEM and UV-vis absorption measurements (UV-visible absorption spectra were recorded using a Agilent Model Cary 5E spectrophotometer, equipped with an integrating sphere DRA 2500). The composition (number of fluorescent molecules in the core and magnetic nanoparticles of the shell) has been determined by both mass spectrometry and magnetic sedimentation.

DLS and TEM measurements of fluo@mag@PAA nanoassemblies yield a mean diameter of 120-150 nm. DLS measurements, performed in water, generally display slightly larger diameters due to the first water solvation sphere. The nanoassemblies are stable in water over a period of 5 months at room temperature and over almost a year at 4° C. The size distribution varies little after lyophilization and redispersion in various media (water, HBSS, PBS, ethanol) as demonstrated by DLS and UV-vis absorption measurements, in accord with parallel DLS and TEM analyses. The fluo@mag@PAA nanoassembly cohesion, ensured by the PAA coating, is also demonstrated by means of ultra-sounds which do not dissociate the nanoassemblies. Mass spectrometry analyses and magnetic sedimentation, enabling the composition determination, show convergent data: the core was made of ~10$^5$ organic molecules (in agreement with previous results involving single nanoparticle photoabsorption measurements), surrounded by a shell of ~10$^4$ maghemite nanoparticles. Relaxivity measurements demonstrate large cooperativity effects between the vicinal iron oxide nanoparticles assembled in the magnetic shell. The threefold increase in the R2/R1 ratio observed for the nanoassemblies allows for highly contrasted T2-weighted MRI. Finally, steady-state and time-resolved fluorescence measurements show that the fluorescence signal is not affected by the surrounding media as expected from the protecting role played by the maghemite nanoparticle shell.

2.1. Size Characterizations

Size characterizations (DLS and TEM measurements) of the fluo@mag@PAA nanoassemblies were carried out after formation, after the lyophilization-redispersion process and after having been subjected to ultra-sounds. After redispersion, no agglomeration is observed by DLS even for solutions with concentrations higher than those of the initial solution before lyophilization. Moreover no nanoassembly dissociation is observed after ultra-sounds.

Figure 3:
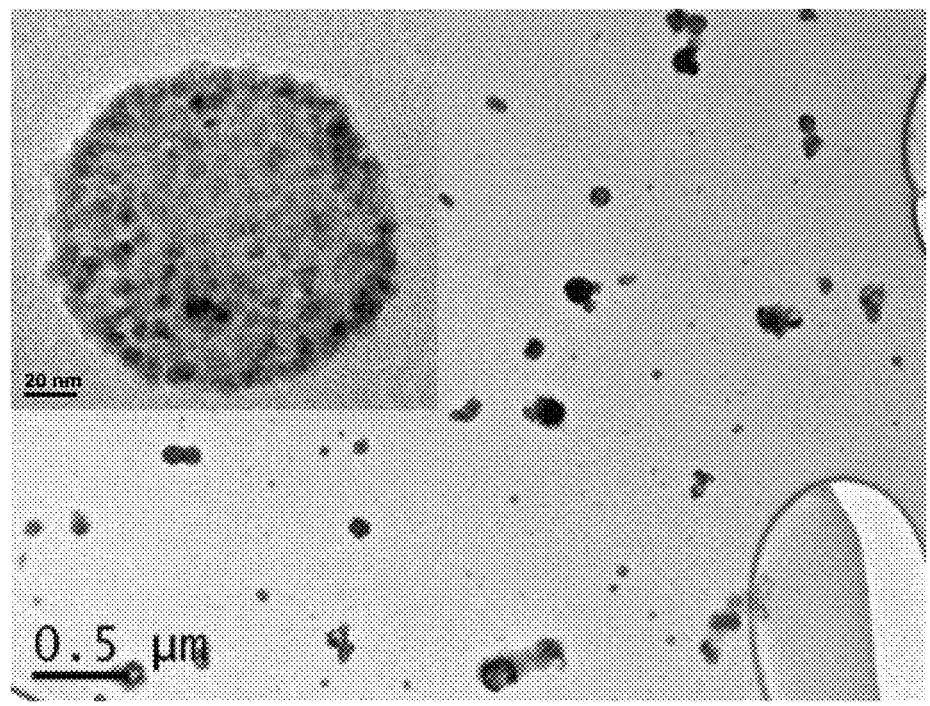
FIG. 3 is a TEM image of fluo@mag@PAA nanoassemblies after synthesis. Inlet: zoom-in with a 20 nm scale bar.

The assemblies characterized by TEM, were deposited on holey carbon grids and dried at room temperature. Observations (FIG. 3) were performed with a MO-Jeol MET 1230, working at a 80 kV voltage.

2.2. Colloidal Stability

The stability of fluo@mag@PAA nanoassemblies was studied as a function of time and in distinct solutions with various pHs and ionic strengths.

DLS and TEM measurements of nanoassemblies dispersed in Millipore water were conducted right after the synthesis and after a few months. The results feature the high stability of the nanoassembly structure (TEM—FIG. 3).

UV-vis absorption analyses were also performed at 450 nm as a function of time to follow the colloidal stability. In the case of unstable dispersions of nanoparticles, sedimentation is usually observed with a loss of absorbance. Absorbance decreases by less than 2% after 11 days, proving the highly stable colloidal character of the nanoassemblies, be they placed in water or redispersed in HBSS or PBS buffer.

The nanoassemblies are stable over a large pH range (3-12) due to a significant surface potential ζ<−31 mV, causing efficient electrostatic repulsions between the nanoassemblies. As a consequence, no aggregation could also be observed in media of varying ionic strength up to 0.3 mol·L$^{-1}$, which is beneficial for biological applications dealing with media usually with high ionic strength.

2.3. Composition Determination

Studies were conducted to determine the amount of iron oxide NPs on the surface of the organic core by means of mass spectrometry and magnetic sedimentation respectively.

Mass spectrometry experiments were realized according to the method described in Doussineau et al., *Rapi. Commun, Mass Spectrom,* 2011, 25, 617-623. The molar mass distributions for the fluorescent nanospheres and the fluo@mag@PAA nanoassemblies were recorded. The noticeable increase in weight (namely 86 MDa) when going from fluorescent organic nanospheres to fluo@mag@PAA nanoassemblies can be mainly correlated to the amount of iron oxide nanoparticles, assessed around $2 \times 10^4$ nanoparticles per nanoassembly. These measurements also confirm the amount of fluorescent molecules per organic core, valued to be around $10^5$ fluorescent molecules.

Magnetic decantation experiments were carried out to analyze the time-evolution of the normalized absorbance at 552 nm and 446 nm. Magnetic sedimentation was performed with solutions of maghemite nanoparticles dispersed in dilute nitric acid (pH=1.2) and solutions of fluo@mag@PAA nanoassemblies dispersed in water.

Comparative measurements of the magnetic sedimentation of single maghemite nanoparticle dispersions and fluo@mag@PAA nanoassembly dispersions show stronger sedimentation with the latter in accord to their higher magnetic content. Modeling the absorbance decay indicated that the magnetic shell of the nanoassembly comprised $\sim 10^4$ maghemite nanoparticles, in agreement with the data obtained by mass spectrometry.

2.4. Relaxivity Measurements

Relaxivity measurements ($^1$H NMR longitudinal T1, and transverse T2 relaxation times) were conducted for the fluo@mag@PAA nanoassemblies in diluted solutions.

Procedure

Figure 4:
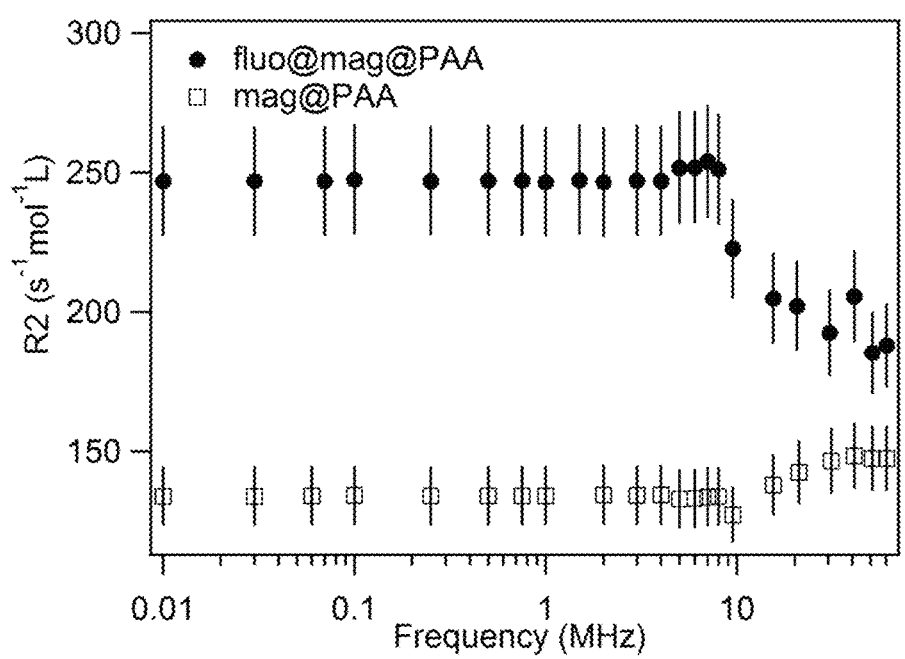
FIG. 4 is the evolution of the transverse relaxivities R2 of fluo@mag@PAA nanoassemblies ($D_H$=150 nm; black dot labels) and dispersed iron oxide nanoparticles coated with PAA (mag@PAA: $D_H$=7 nm; white square labels) as a function of frequency. Vertical bars represent measure errors.
Figure 5:
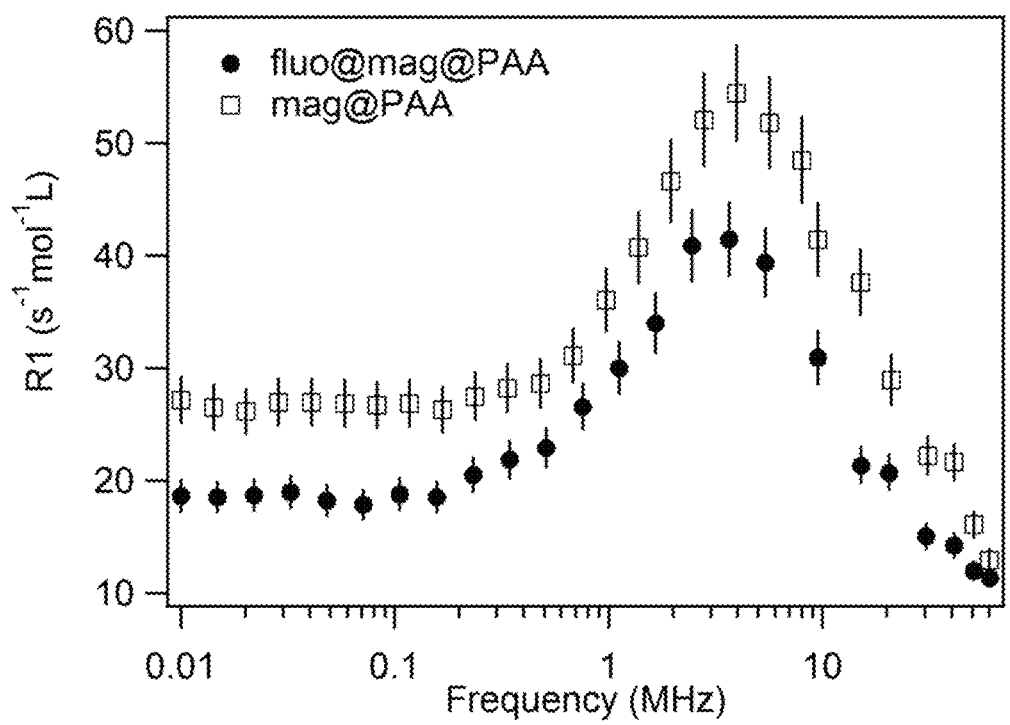
FIG. 5 is the evolution of longitudinal relaxivities R1 of fluo@mag@PAA nanoassemblies ($D_H$=150 nm; black dot labels) and dispersed $\gamma$-$Fe_2O_3$ nanoparticles coated with PAA (mag@PAA: $D_H$=7 nm; white square labels) as a function of frequency. Vertical bars represent measure errors.

Measurements of $^1$H longitudinal T1 and transverse T2 relaxation times at different frequencies ν at room temperature were performed on diluted solutions of samples (at ν=200 and 300 MHz), in the range of 10 kHz≤ν≤212 MHz for T1 and 15 MHz≤ν≤60 MHz for T2. Proton T1 and T2 relaxation time measurements were performed on aqueous solutions with different concentrations of nanoassemblies at room temperature (300 K) under an applied magnetic field of 4.7 T using a Tecmag Apollo spectrometer operating at 200 MHz. The rates observed for both longitudinal and transverse relaxations showed a linear dependence according to the nanoparticle concentration. Using the inversion-recovery and spin echo (Can-Purcell Meiboom Gill) sequences to measure T1 and T2, the longitudinal R1 and transverse R2 relaxivities were calculated from the slope of the plot of 1/T1 and 1/T2 curves vs nanoparticle concentration. FIGS. 4 and 5 feature the transverse and longitudinal relaxivities respectively, as a function of frequency, of fluo@mag@PAA nanoassemblies and dispersed iron oxide nanoparticles coated with PAA.

Higher values of transverse relaxivity R2 are obtained for fluo@mag@PAA nanoassemblies compared to those of dispersed iron oxide nanoparticles. The longitudinal relaxivity R1 varies in the opposite trend. The high values of T2 and the large increase in the R2/R1 ratio for the nanoassemblies, related to the T2 weighted MRI, demonstrate the very positive cooperative effects between the iron oxide nanoparticles at the surface of the nanoassemblies. Such a cooperativity does not exist for isolated iron nanoparticles serving as a reference.

2.5. Photophysical Properties

Figure 6:
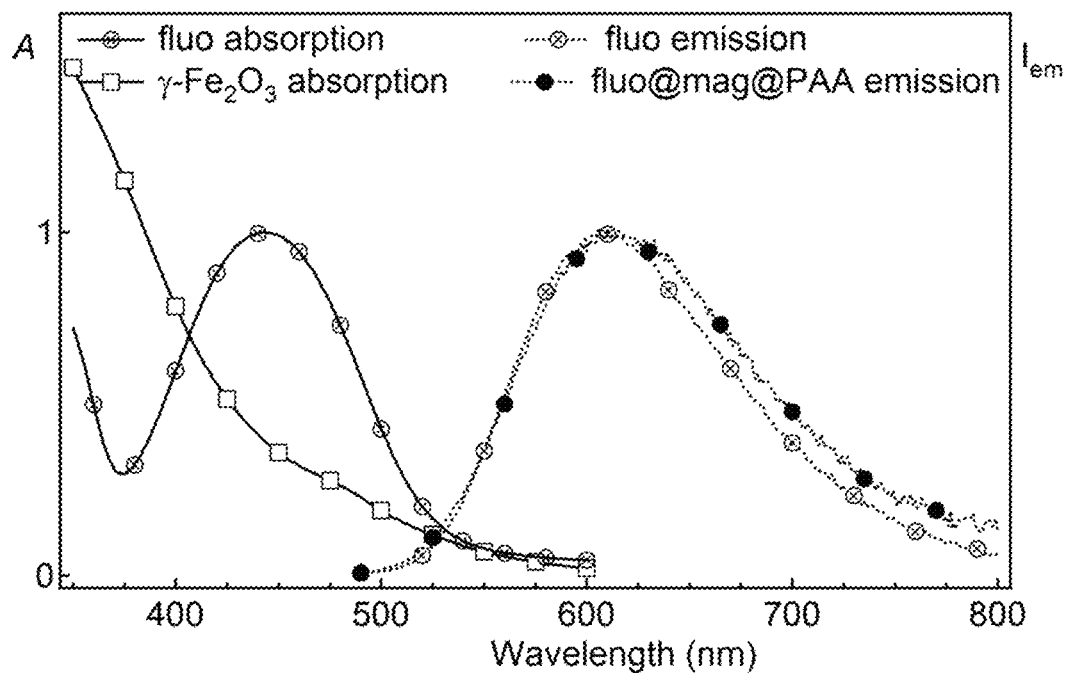
FIG. 6 UV-vis absorption spectra in water of the fluorescent organic nanoparticles (fluo absorption) and $\gamma$-Fe$_2$O$_3$ nanoparticles ($\gamma$-Fe$_2$O$_3$ absorption) and emission spectra ($\lambda_{exc}$=450 nm) of the fluorescent organic nanoparticles (fluo emission) of fluo@mag@PAA nanoassemblies (fluo@mag@PAA emission).

Steady-state absorption and emission measurements (FIG. 6), time-resolved fluorescence measurements, and wide-field fluorescence microscopy of fluo@mag@PAA nanoassemblies dispersed in various media were realized to characterize their emission intensity and spectral range.

TABLE 2

Photophysical characteristics of fluo@mag@PAA nanoassemblies dispersed in water.

| $\lambda_{max}$(abs) [nm] | $\lambda_{max}$(em) [nm] | $\tau_1(f_1)^1$ [ns] | $<\tau_s>^2$ [ns] |
|---|---|---|---|
| 443 | 604 | 0.7 (29%), 0.2 (52%), 0.04 (19%) | 0.31 |

[1]After laser excitation at 450 nm and detection at 580 nm.
[2]The intensity averaged time constant $<\tau_s>$ and normalized time fractional amplitude $f_i$ are calculated from global analysis using a multiexponential fit $I(t) = \sum_i [a_i \exp(-t/\tau_i)]$ with $a_i$ pre-exponential factor. The intensity-averaged time constant $<\tau_s>$ is defined as $(\tau_s) = \sum_i f_i \tau_i$ with $f_i = a_i \tau_i / \sum_j a_j \tau_j$.

No significant effect of the presence of the PAA coating on the emission properties could be observed compared to the non-stabilized fluo@mag nanoparticles. The fluorescence signal is also insensitive to the nature of the surrounding solutions. This permits accurate detection of the nanoparticles in biological media, requesting no change in the fluorescence intensity or color unless specifically expected. Efficient fluorescence signal is detected upon exciting the fluo@mag@PAA in the absorption band of the fluorescent core. The red-shifted emission compared to the maghemite nanoparticle absorption band avoids deleterious emission reabsorption by the maghemite nanoparticles (FIG. 6), although a small decrease in the emission intensity of the core compared to that of neat fluorescent nanospheres could be noticed. This effect is due to electron transfer from the core to iron (III) ions of the maghemite nanoparticles. Such an emission quenching is actually much stronger for the normal or doped architectures usually reported in literature, where each peripheral fluorescent unit is in direct contact with the iron oxide nanoparticles.

3. In Vitro Experiment

Two different lines of human cells (HEK 293 and MDA-MB-468) are used as well-known model cells for in vitro studies to investigate the uptake of nanoassemblies and their cytotoxicity effects. Fluorescence microscopy and TEM imaging are performed to characterize the fluorescence properties and the arrangement of the nanoassemblies inside the cells.

Cell uptake of the nanoassemblies operates within 6-8 h. Cytotoxicity MTT assays reveal that cell viability is not hampered following cell culture with a 15 μmol·$L^{-1}$ Fe concentration, similar to those used for in vivo MRI experiments. Fluorescence microscopy imaging of live cells shows mobile orange bright spots inside the cells, proving no significant aggregation of the internalized nanoparticles. Comparison experiments with fluorescent organic nanospheres prove that the nanoassemblies do not dissociate within the cells since high structural stiffness is brought by the PAA coating. These results are corroborated by 2D TEM imaging of cells showing the intact structure of the nanoassemblies and the circular arrangement of the iron oxide nanoparticles around the organic core.

3.1. Procedures

Cell Incubation

The cells were incubated for at least 24 h on an Ibidi 8-well plate at 37.7° C. in a 5% $CO_2$ atmosphere. 5000 cells were incubated for experiments running over 72 h. MDA cells were grown in RPMI media containing 10% of fetal bovin serum and 1% of penicillin and streptomycin. HEK cells were grown in DMEM media (high glucose, with glutamine) containing 10% of fetal bovin serum and 1% of penicillin and streptomycin.

Nanoassembly Internalization

Internalization was performed by adding to the cell medium a solution of fluo@mag@PAA nanoparticles dispersed in water (10-20 µL) such that the final concentrations of fluorescent molecules and iron were about $1 \times 10^{-6}$ mol·L$^{-1}$ and $2 \times 10^{-5}$ mol·L$^{-1}$. The suspension was incubated for 6 h to ensure efficient cell uptake of the nanoassemblies, which could already be observed after 3 h only.

3.2. Cell Viability

Viability Assays (MTT Assay)

5000 cells were grown in the appropriate culture medium (200 µL) for 24 h. They were then incubated for various periods of time with a solution of fluo@mag@PAA nanoassemblies dispersed in Millipore water. The cell viability was evaluated by using MTT assays. A solution of MTT (20 µL; 5 mg·mL$^{-1}$) was added to the cells which were incubated for a further 2 h-2 h 30. The supernatant solution was removed and DMSO (200 µL) was added to dissolve the colored oxidized product. Absorbance read-out at 570 nm provides viability of the incubated cells by comparison with reference cells.

The MTT assays reveal almost no cell cytotoxicity for nanoassembly solutions with a 15 µmol·L$^{-1}$ iron content (cell viability>95%) which is the common concentration used for all in vitro and in vivo experiments. For very large concentrations of iron (300 µmol·L$^{-1}$), only the HEK cells exhibit significant mortality in agreement with an increase in the oxidative stress caused by the large excess of iron (300-500 µg·mL$^{-1}$).

3.3. Fluorescence Microscopy of Internalized Nanoassemblies in Live Cells

Fluorescence microscopy was performed in the confocal mode by means of a LSM working in the inverted mode (Nikon MR Si, oil-immersion objective Plan Apo, ×60, 1.4, $\lambda_{exc}$=488 nm), or in the wide-field mode by means of an inverted microscope (Nikon Eclipse Ti, oil-immersion objective Plan Apo, ×60, 1.4, $\lambda_{exc}$=482 nm).

Figure 7:
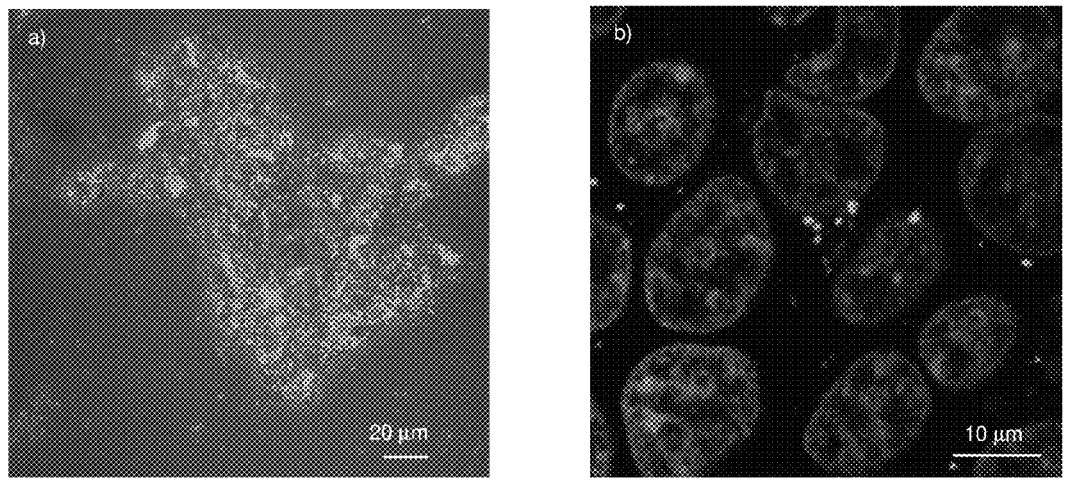
FIG. 7 is fluorescence confocal laser scanning microscopy images of HEK cells incubated with fluo@mag@PAA nanoassemblies at: a) a 3 µM concentration of fluorescent molecules with no staining agent ($\lambda_{exc}$=488 nm, $\lambda_{em}$>510 nm), b) a 1 µM concentration of fluorescent molecules and post-treated with a nucleus staining agent (Hoechst 33342) ($\lambda_{exc}$=405 nm, $\lambda_{em}$>510 nm) (objective ×63, NA 1.4).

Internalized nanoassemblies can clearly be distinguished as spots on FIG. 7a without undergoing significant aggregation inside the cells. No spots can be distinguished inside the nuclei, indicating that the nanoassemblies stay in the cytoplasm and do not penetrate into the nuclei (FIG. 7b).

TEM Imaging of Internalized Nanoassemblies

Procedure

Addition of HEK cells in agar solution at 45-50° C.;
Fixation for 2 h at 4° C. of small pieces of agar gel using a phosphate 0.1 M solution and 3% glutaraldehyde;
Washing with phosphate buffer and Millipore water;
Post-staining using osmium tetroxide (1%) in Millipore water for 1 h and repeated washings using Millipore water;
Dehydration using an ethanol bath for 1 h with increasing concentration in ethanol (30%, 50%, 70%, 85%, 95%, 100%);
Dehydration using a 100% ethanol bath (2 h and overnight at 4° C.);
Exchange of ethanol with propylene oxide;
Inclusion in EPON resine;
Polymerization for 1 day at 55° C. and 60 h at 72° C.;
Staining after slicing for 30 min in uranyl acetate and washing using Millipore water.

Figure 8:
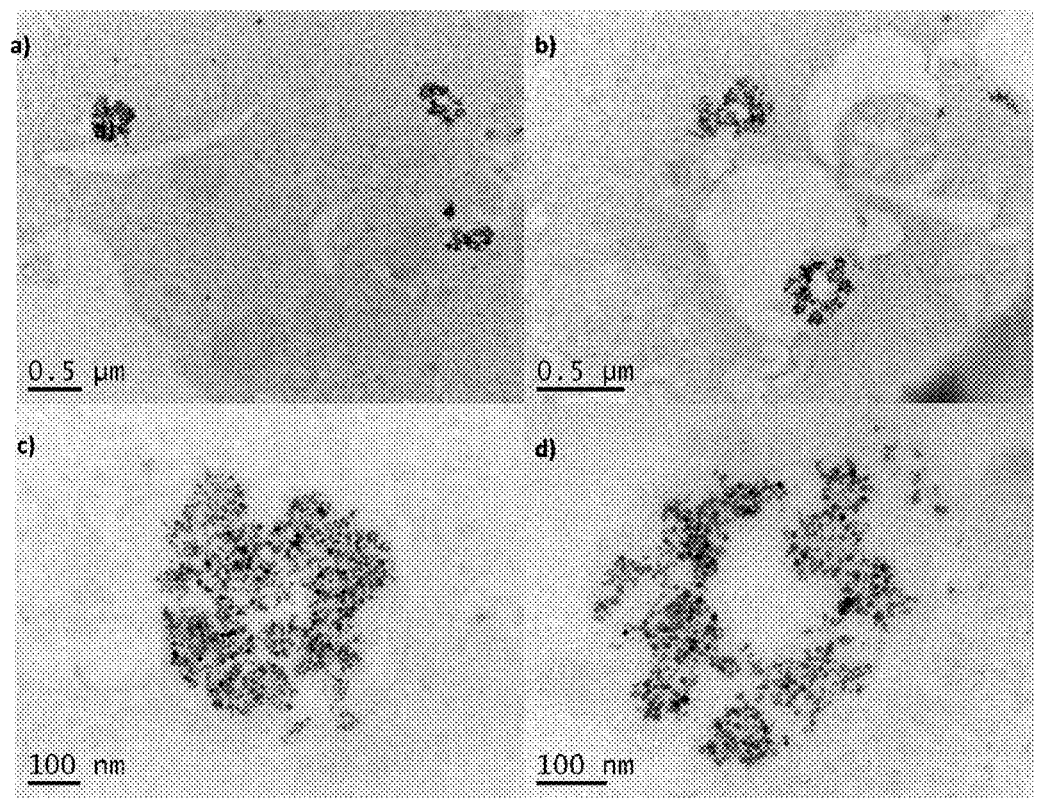
FIG. 8 is TEM images of internalized nanoparticles in HEK cells (70 nm-thin section). a) General view. b) Zoom-in view. c) and d) Endosomes trapping the fluo@mag@PAA nanoassemblies.

TEM imaging (FIG. 8) reveals the embedment of contrasted iron oxide nanoparticles in cell endosomes after cell uptake. Remarkably, the maghemite nanoparticles are organized following a disk-like arrangement recalling the spherical core-shell structure of the nanoassemblies. Given the strong fluorescence detectable in live cells, these TEM images show that the nanoassemblies keep their integrity after internalization with no dissociation of the magnetic shell from the organic core thanks to the cohesive PAA coating.

4. In Vivo Experiments

In vivo Magnetic Resonance Imaging is performed on a series of 5 mices. After mice euthanasia, the extracted organs are sliced for fluorescence microscopy imaging using one- and two-photon excitation to minimize tissue auto-fluorescence.

Five mice (mouse 1-5) are injected with a low dose of fluo@mag@PAA nanoassemblies (250 µL, 1.3 µmol·mL$^{-1}$ Fe concentration) compared to literature. T2-weighted MRI experiments are focused on the main organs (spleen and liver) responsible for most of the nanoassembly clearance through the recruitment of macrophages for 150 nm-sized nanoparticles. A clear decrease in the T2* contrast in the liver and spleen can be observed 20-25 min after the injection. These observations feature efficient uptake of the nanoassemblies. They also demonstrate the efficient role of the fluo@mag@PAA nanoassemblies as MRI contrast agents despite the low Fe concentration used. They are to be linked to the high R2/R1 ratio of the longitudinal R1 and transverse R2 relaxivities (see Point 2.4.). Fluorescence microscope imaging clearly distinguishes fluo@mag@PAA nanoassemblies as bright emitting spots in the sliced tissues with no penetration in the cell nuclei. The fluo@mag@PAA nanoassemblies efficiently respond to two-photon excitation, allowing for higher localization resolution and NIR investigations in the tissue transparency window. In agreement with the clearance process, the non-functionalized fluo@mag@PAA nanoassemblies mostly accumulate in the liver, and in the spleen to a lesser extent. Very few nanoassemblies are found in the kidneys responsible for the clearance of smaller nanoparticles (a few nm-sized) while none of them is found in the lung and heart.

4.1. Magnetic Resonance Imaging on Small Rodents

Figure 9:
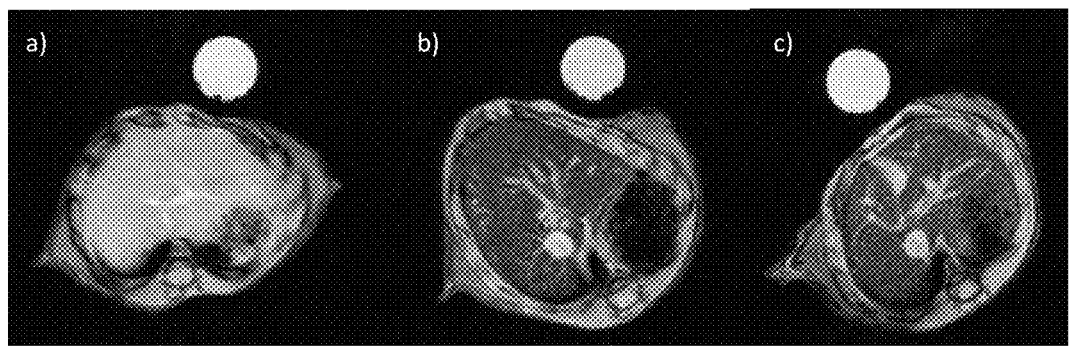
FIG. 9 is T2*-weighted MR images of mouse 1's liver. a) before the injection, b) 25 min after the injection, c) 230 min after the injection. The white circle corresponds to a water magnetic resonance phantom.
Figure 10:
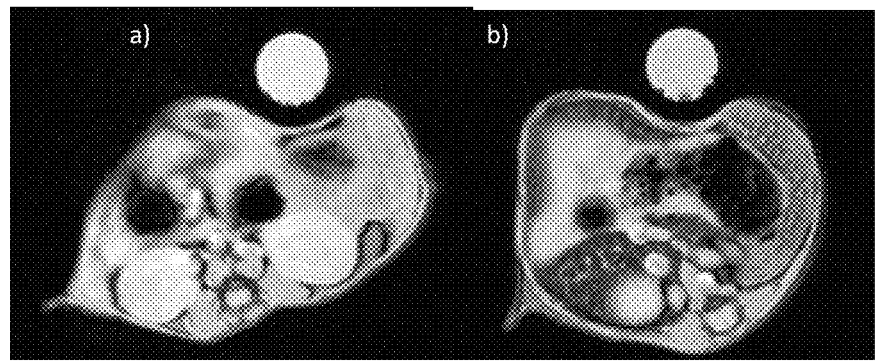
FIG. 10 is T2*-weighted MR images of mouse 1's spleen. a) before the injection, b) 25 min after the injection. The white circle corresponds to a water magnetic resonance phantom.

MRI imaging has been performed in order to observe magnetic cooperativity between the iron oxide nanoparticles on the surface of the nanoassembly. As shown on FIGS. 9 and 10, a negative contrast has been obtained by T2* imaging with iron concentrations lower that those commonly used with individual iron oxide nanoparticles (average concentration in the literature: 40-70 µmol Fe/kg). No contrast evolution was observed after 3 h 50 after injection Procedure T2 weighted MRI experiments (FIGS. 9-10) were performed on 5 female BALB/C mice (5-week old) by means of a MRI spectrometer BioSpect 4.7 T (Bruker). The echo time TE and the repetition time TR of the sequence (T2* mode) were set at 5 ms and 300 ms respectively. A concentration of 13 µmol Fe/kg mouse was chosen to perform these analyses.

The mouse was anesthetized using isofluorane gas at a concentration allowing for 30 heartbeats per minute. Images of the liver were recorded as references before injecting the nanoassemblies. A suspension of fluo@mag@PAA nanoassemblies in HBSS buffer (250 µL, 1.3 µmol·mL$^{-1}$ Fe concentration) was injected in the mouse caudal vein. MRI was performed after 20-30 min. An average spleen ENH of −13% and liver ENH of −49% was obtained.

4.2. Fluorescence Microscopy of Sliced Tissues
4.2.1. Tissue Sectioning Procedure The mice were sacrificed 24 h after the injection. Five organs (liver, spleen, kidney, lung and heart) were removed for ex vivo analyses in order to assess the biodistribution of the fluo@mag@PAA nanoassemblies. They were successively immersed in a bath of zinc-containing fixatives (Pharmingen, France) at 4° C. for 48 h, and 4 wt. % paraformaldehyde –20 wt. % sucrose solution at 4° C. for 24 h. They were eventually frozen in OCT (Tissue-Tek) by using vapors of liquid nitrogen Zinc-containing fixatives avoid fainting of the fluorescent molecules during the fixing process. The frozen organs were stored at –80° C. for 30 days before use. They were cut in 10 μm-thick sections at –20° C. using a cryotome cryostat (Leica Biocut 2030). The sections were immediately deposited on superfrost glass slides, let dry for 2 h before being treated with Prolong (containing or not DAPI as a cell nucleus staining agent) and protected with an upper coverslit to allow for microscopy imaging. The sections were left at 4° C. for at least 72 h before observation.

4.2.2. Instrumentation

Fluorescence microscopy was performed in the confocal mode by means of two kinds of LSM working in the inverted mode:
- one-photon fluorescence imaging: Nikon A1R Si equipped with Ar$^+$ and He—Ne lasers as excitation sources (use of an oil-immersion objective Plan Apo, ×60, 1.4, $\lambda_{exc}$=488 nm)—collaboration IRSUN/Nantes;
- two-photon fluorescence imaging: Zeiss LSM 780 equipped with a tunable Ti:sapphire femtosecond laser (Mai Tai, 710-920 nm) and a 32-channel QUASAR GaAsp detector allowing for multispectral imaging. All images were acquired upon excitation at 830 nm and using two detection channels (blue centered at 450 (±35) nm and red centered at 654 (±104) nm)—collaboration KU Leuven/Belgique.

Despite the strong autofluorescence displayed by highly pigmented tissues like liver or spleen, emission of the nanoassemblies was clearly distinguished under one- or two-photon excitations. The nanoassemblies appear as localized small and very bright spots with a fluorescence signal centered at 580 nm, neatly red-shifted compared to the 520 nm-centered autofluorescence. The spot dimensions, close to those of a single nanoassembly, taking into account light scattering, lets us suggest the absence of nanoassembly aggregation or dissociation in vivo. Fluorescence microscope imaging reveals that the nanoassemblies do not enter the hepatocyte cell nuclei. The nanoassemblies exhibit no significant bleaching under normal observation conditions in contrast with the tissue auto-fluorescence, which should enable accurate localization of the nanoassemblies when properly functionalized with targeting agents.

5. Supplementary—Functionalization by Biologically Active Agents

The fluo@mag and fluo@mag@PAA nanoassemblies could be coated with biologically-active molecules like folic acid (FA) or aminocoumarine, serving as accelerators of cell internalization of nanoparticles and antibiotics respectively. Folic acid was chosen for its complexing carboxylic unit toward the external layer of iron oxide nanoparticles while the aminocoumarine displayed an amino function, amenable to covalently bind the fluo@mag@PAA surface through amide bond formation.

Complexation of the bimodal fluo@mag nanoassemblies with FA could be realized provided that the resulting nanoassemblies fluo@mag@FA are stored in the dark at 4° C. Additional conjugation has then been tested with the fluo@mag@PAA nanoassemblies the surface of which was covalently linked to a fluorescent probe 7-amino-4-methylcoumarin (AC) through amide bond formation. Steady-state and time-resolved fluorescence measurements performed on the resulting architectures fluo@mag@FA and fluo@mag@PAA-AC allowed us to confirm the tight FA and AC grafting at the surface of the nanoassemblies and showed the superiority of fluo@mag@PAA over fluo@mag in terms of surface binding stability of biologically active molecules. Such a functionalization represents the prelude of further grafting of more complex active biomolecules.

5.1. Synthetic Procedure

Complexation of Fluo@Mag Nanoassemblies with Folic Acid

A solution of fluorescent compound (Ib) dissolved in THF (50 μL, 0.1 wt. %) was added under vigorous stirring to a solution of maghemite nanoparticles in nitric acid (2.5 mL, 0.006 wt. %, pH=1.2). After a few seconds, the magneto-fluorescent fluo@mag were formed. Folic acid (>5 eq, 1 mg) was added to the mixture, followed by the dropwise addition of ammonium hydroxide (1 mol·L$^{-1}$) under magnetic stiffing until pH=8 was reached. The resulting translucent solution was allowed to stir for a further 30 min. and dialyzed using a Spectra Por membrane (Standard Grade Regenerated Cellulose; cut-off: 8-10 kDa) against Millipore water (600 mL) over 3-4 h to remove the excess of folic acid. Once the fluo@mag nanoparticles started agglomerating, the dialysis was performed in the presence of trisodium citrate salt (50 mmol·L$^{-1}$) for a few hours. A final dialysis step was performed against Millipore water (600 mL) to remove the excess of citrate ions. The resulting functionalized fluo@mag@FA nanoassemblies were stored at 4° C. to avoid decomplexation of the folic acid units over time.

Covalent Conjugation of Fluo@Mag@PAA Nanoassemblies with 7-Amino-4-Methylcoumarin Dilute nitric acid (pH=1.2) was added to a solution of fluo@mag@PAA assemblies, dispersed in Millipore water (0.7 μmole Fe, <1 μmole PAA, 2.5 mL) until pH=4 was reached. N-(3-dimethylaminopropyl)-N'-ethylcarbodiimide hydrochloride (10 eq, 1.4 mg, 10 μmol) and N-hydroxysuccinimide (10 eq, 1.1 mg, 10 μmol) were added to the mixture under vigorous stiffing using a vortex. The nanoassemblies were stirred for an extra 2 h before adding ammonium hydroxide (1 mol·L$^{-1}$) until pH=9 was reached. Then, 7-amino-4-methylcoumarin (40 eq, 7.0 mg, 40 μmol) was added to the nanoparticle dispersion and the resulting solution was stirred for a further 16 h. The resulting translucent solution was dialyzed using a Spectra Por membrane (Standard Grade Regenerated Cellulose; cut-off: 8-10 kDa) against Millipore water (600 mL) over 72 h until no more blue fluorescent emission was observed in the dialysis bath. The functionalized fluo@mag@PAA-AC nanoassemblies were stored at 4° C.

5.2. Photophysical Characterizations

Fluo@Mag@FA

Complexation of FA on fluo@mag nanoparticles could be detected using steady-state and time-resolved fluorescence measurements. Strong emission fluo@mag quenching of the blue fluorescent FA was observed after complexation to the fluo@mag nanoparticles due to fast electron transfer from the FA excited state to the iron oxide nanoparticles. By contrast, no significant blue emission quenching could be detected when folic acid was simply mixed with a suspension of iron oxide γ-Fe$_2$O$_3$ due to partial complexation only. These results thus demonstrated the cooperative complexing behaviors of ensembles of iron oxide nanoparticles with regard to isolated maghemite nanoparticles. Compared to the tight PAA coating on fluo@mag nanoparticles, FA decomplexation however occurred over time. Detection of a strong blue signal thus features uncomplexed FA and has been harnessed to show the release of folic acid in live cells after incubation for 72 h. These results open the possibility to use the fluo@mag and fluo@mag@PAA nanoassemblies as drug cargos when properly functionalized.

Fluo@Mag@PAA-AC

Figure 11:
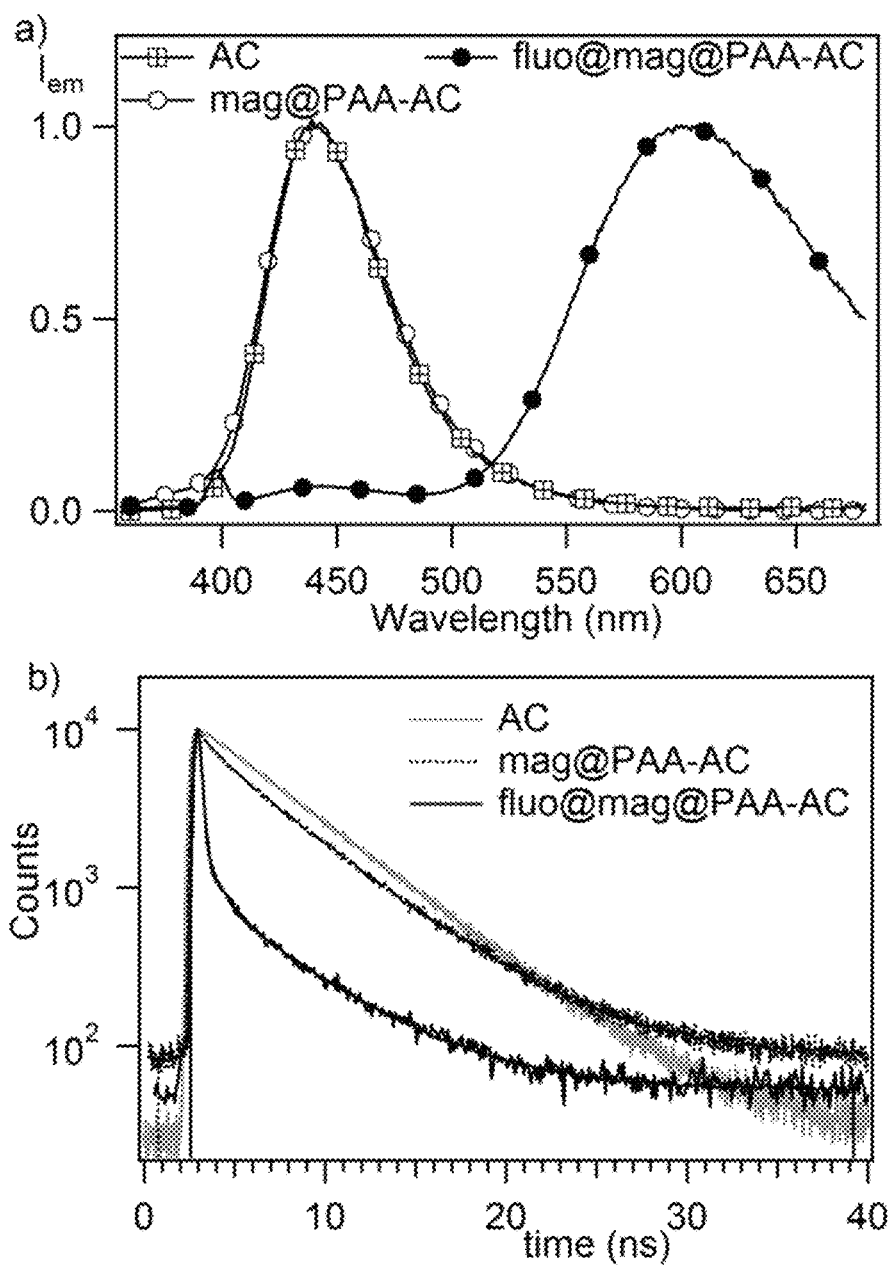
FIG. 11 Comparative emission spectra ($\lambda_{exc}$=350 nm) and fluorescence decays ($\lambda_{em}$=340 nm, $\lambda_{em}$=440 nm) in water of 7-amino-4-methylcoumarine (AC), fluo@mag@PAA-AC nanoassemblies issued from the surface functionalization of fluo@mag@PAA with AC, and mag@PAA-AC issued from the surface functionalization of mag@PAA with AC.

Steady-state and time-resolved fluorescence experiments were also performed to characterize the surface grafting of 7-amino-4-methylcoumarin, displaying a fluorescence signal at 441 nm (FIG. 11). Strong emission quenching was detected (decrease in the fluorescence signal and fluorescence decay) for the AC immobilized on the surface of fluo@mag@PAA nanoassemblies, compared to water solutions of AC only. This quenching effect was ascribed to efficient energy transfer from the AC excited state to the fluorescent organic core due to spectral overlap between the AC emission spectrum and the fluorescent core's absorption spectrum. The fast component observed in the fluorescence decay for fluo@mag@PAA-AC stems from the close proximity of AC toward the iron oxide nanoparticles and consequently to the covalent binding of AC. (FIG. 11b). No such quenching effect was indeed observed when AC was immobilized on the surface of mag@PAA nanoparticles dispersed in water. This experiment definitely shows that covalent attachment of AC to the fluo@mag@PAA nanoassemblies has been achieved since the distance between an energy donor and an energy acceptor must be shorter than 10 nm for efficient energy transfer. Finally no leakage of the covalently linked AC was detected over a period of two weeks. This experiment represents a first step toward the bioconjugation of biologically-active objects proteins for targeted bioimaging and drug delivery.

5.3. Fluorescence Microscopy Imaging of Live Cells

HEK cells were incubated with folic acid-coated fluo@mag nanoassemblies (fluo@mag@ FA) and observed by wide-field fluorescence microscopy.

The fluo@mag@FA were efficiently internalized in HEK cells. They provide blue emission after 72 h of incubation as a result of the decomplexation of folic acid whereas no such operates after 20 h only. Green emission instead of an orange one is to be related to the disassembling process of fluo@mag nanoassemblies since there is no PAA coating, known to ensure tight cohesion.

The invention claimed is:

1. A nanoassembly comprising:
   one single fluorescent core comprising fluorescent organic molecules, and
   magnetic nanoparticles contacting the surface of said fluorescent core;
   wherein the fluorescent core does not comprise a polymer or silica; and
   wherein the nanoassembly has a hydrodynamic diameter ranging from 20 to 800 nm.

2. The nanoassembly according to claim 1, wherein the fluorescent organic molecules are compounds of Formula I,

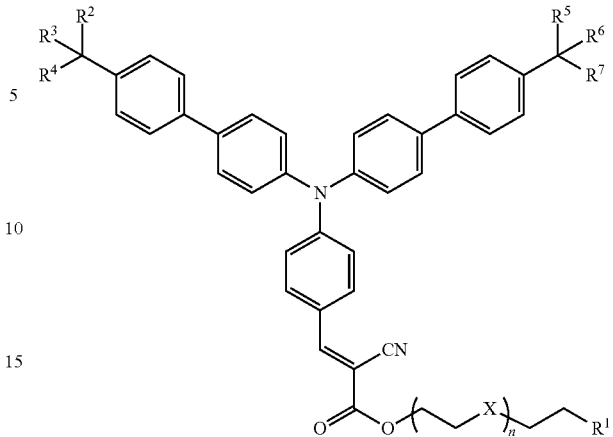

wherein:
X represents O or $CH_2$;
n represents an integer selected from 1, 2, 3 and 4;
$R^1$ represents —$CO_2H$ or —$P(O)(OH)_2$;
$R^2$, $R^3$, $R^4$, $R^5$, $R^6$ and $R^7$ represent each independently an optionally functionalized group selected from alkyl and ester or polyethylene glycol, preferably $R^2$, $R^3$, $R^4$, $R^5$, $R^6$ and $R^7$ represent each a methyl group.

3. The nanoassembly according to claim 1, wherein the magnetic nanoparticles are superparamagnetic nanoparticles selected from the group comprising $\gamma$-$Fe_2O_3$ and $Fe_3O_4$.

4. The nanoassembly according to claim 1, having a hydrodynamic diameter ranging from 20 to 700 nm.

5. The nanoassembly according to claim 1, wherein the fluorescent core comprises a number of organic fluorescent molecule ranging from $1 \times 10^4$ to $1 \times 10^7$.

6. The nanoassembly according to claim 1, comprising a number of magnetic nanoparticles ranging from $1 \times 10^2$ to $1 \times 10^6$.

7. The nanoassembly according to claim 1, further comprising at least one polymer contacting at least one of the magnetic nanoparticle or the surface of the core.

8. The nanoassembly according to claim 7, wherein the polymer is an ionic polymer, preferably a polyelectrolyte.

9. The nanoassembly according to claim 7, wherein the polymer is of Formula II,

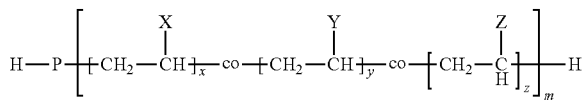

wherein,
m represents a positive integer ranging from 20 to 150;
x, y and z represent each independently a percentage of m, ranging from 0% to 100% of m, wherein x+y+z is equal to 100% of m;
X represents —COOH, alkyl, aryl; Y represents —(C=O)—O-$L^1$-$R^8$, —(C=O)—S-$L^1$-$R^8$, —(C=O)—NH(-$L^1$-$R^8$) or —(C=S)—NH(-$L^1$-$R^8$)
wherein
$L^1$ represents a spacer selected from alkyl, alkene, aryl, arylalkyl, polyethylene glycol or polypropylene glycol linking groups having 1 to 150 chain atoms, wherein the linking group can be optionally interrupted or terminated by one or more —O—, —S—, —NR$^9$—, —CO—, —NHCO—, —CONH— or a combination thereof, wherein R$^9$ is H or alkyl;

R$^8$ represents a reactive group selected from N$_3$, amino, alkylamino, COOH, amide, maleimide, alkyne, SH, OH, ester, activated ester, activated carboxylic acid, halo, nitro, nitrile, isonitriles, acrylamide, aldehyde, ketone, acetals, ketals, anhydride, glutaric anhydride, succinic anhydride, maleic anhydride, thiocyanate, isothiocyanate, isocyanate, hydrazide, hydrazines, hydrazones, ethers, oxides, cyanates, diazo, diazonium, sulfides, disulfides, sulfoxides, sulfones, sulfonic acids, sulfinic acids, sulfates, sulfenic acids, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, acetylene, olefins, polyenes, alkylacrylates, oxetane, ammoniums, oxoniums, phosphoniums, sulfoniums, positively charged metal complexes;

Z represents —(C=O)—O-L$^2$-R$^{10}$, —(C=O)—S-L$^2$-R$^{10}$, —(C=O)—NH(-L$^2$-R$^{10}$) or —(C=S)—NH(-L$^2$-R$^{10}$) wherein L$^2$ represents a single bond or a spacer selected from alkyl, alkene, aryl, arylalkyl, polyethylene glycol or polypropylene glycol linking groups having 1 to 150 chain atoms, wherein the linking group can be optionally interrupted or terminated by one or more —O—, —S—, —NR$^9$—, —CO—, —NHCO—, —CONH— or a combination thereof, wherein R$^9$ is H or alkyl; optionally additionally comprising a residue of a reactive group through which L$^2$ is bonded to R$^{10}$;

R$^{10}$ represents a bioactive group selected from amino acid, peptide, protein, antibody, enzyme, polysaccharide, dextran, benzylguanine, lipid, lipid assembly, fatty acid, nucleoside, nucleotide, oligonucleotide, hapten, aptamer, ligand, substrate, biotin, avidin, synthetic polymer, polyethylene glycol, polypropylene glycol, polymeric microparticle, nanoparticle, fluorophore, chromophore, radioisotope, macrocyclic complexes of radioisotope, and combinations thereof.

10. The nanoassembly according to claim 7, wherein the polymer is polyacrylic acid.

11. The nanoassembly according to claim 7, having a hydrodynamic diameter ranging from 50 to 800 nm.

12. A pharmaceutical composition comprising the nanoassembly according to claim 1, in combination with at least one pharmaceutically acceptable vehicle.

13. A medicament comprising the nanoassembly according to according to claim 1.

14. A pharmaceutical composition comprising the nanoassembly according to claim 7, in combination with at least one pharmaceutically acceptable vehicle.

15. A medicament comprising the nanoassembly according to according to claim 7.

* * * * *